US007863004B2

(12) United States Patent
Tainsky et al.

(10) Patent No.: US 7,863,004 B2
(45) Date of Patent: Jan. 4, 2011

(54) NEOEPITOPE DETECTION OF DISEASE USING PROTEIN ARRAYS

(75) Inventors: Michael A. Tainsky, Detroit, MI (US); Sorin Draghici, Detroit, MI (US)

(73) Assignee: Wayne State University, Detroit, MI (US)

( * ) Notice: Subject to any disclaimer, the term of this patent is extended or adjusted under 35 U.S.C. 154(b) by 29 days.

(21) Appl. No.: 10/004,587

(22) Filed: Dec. 4, 2001

(65) Prior Publication Data
US 2004/0005556 A1 Jan. 8, 2004

(51) Int. Cl.
G01N 33/53 (2006.01)
G01N 33/48 (2006.01)
A61K 39/385 (2006.01)
A61K 39/395 (2006.01)

(52) U.S. Cl. .................. 435/7.1; 424/130.1; 424/193.1; 436/64

(58) Field of Classification Search .................. 702/19; 436/64; 435/6, 7.1; 706/13
See application file for complete search history.

(56) References Cited

U.S. PATENT DOCUMENTS 5,670,312 A * 9/1997 Santi .............................. 506/4
2003/0003516 A1 * 1/2003 Robinson et al. ............. 435/7.9

FOREIGN PATENT DOCUMENTS

WO    WO 99/39210    *    8/1999

OTHER PUBLICATIONS

The NEB Transcript (1996) vol. 8, No. 1, pp. 1-6.*
Sioud et al. (European Journal of Immunology (2001) vol. 31, pp. 716-725).*
Alizadeh, AA. et al., "Distinct Types of Diffuse Large B-cell Lymphoma Identified by Gene Expression Profiling," *Nature*, 403:503-511 (2000).
An, A, et al., "A Learning System for More Accurate Classifications," *Lecture Notes in Artificial Intelligence*, 1418:426-441 (1998).
Aunoble, B. et al., "Major Oncogenes and Tumor Suppressor Genes Involved in Epithelial Ovarian Cancer," *Int J Oncol* 16:567-76 (2000).
Baron, A.T. et al., "Serum sErbB1 and Epidermal Growth Factor Levels As Tumor Biomarkers in Women with Stage III or IV Epithelial Ovarian Cancer," *Cancer Epidemiology, Biomarkers & Prevention* 8:129-137 (1999).
Bast, R.C. et al., "A Radioimmunoassay Using a Monoclonal Antibody to Monitor the Course of Epithelial Ovarian Cancer," *N Engl J Med*, 309: 883-887 (1983).
Bast, R.C. et al., "Reactivity of a Monoclonal Antibody with Human Ovarian Carcinoma," *J. Clin Invest*, 68:1331-1337 (1981).
Bauer, R. et al., "Cloning and Characterization of the Drosophila Homologue of the AP-2 Transcription Factor," *Oncogene* 17:1911-1922 (1998).

Bittner, M. et al., "Molecular Classification of Cutaneous Malignant Melanoma by Gene Expression Profiling," *Nature*, 406:536-540 (2000).
Blake, C. et al., "UCI Machine Learning Respitory Content," (1998).
Boyd, J. et al., "Hereditary Ovarian Cancer: Molecular Genetics and Clinical Implications," *Gynecol Oncol* 64:196-206 (1997).
Breiman, L. et al., "Classification and Regression Trees," *Wadsworth and Brooks* (1984).
Chiao, P.J. et al., "Elevated Expression of the Ribosomal Protein S2 Gene in Human Tumors," *Molecular Carcinogenesis*, 5:219-231 (1992).
Clark, P. et al., "The CN2 Induction Algorithm," *Machine Learning*, 3:261-283 (1989).
Coleman, M.P., et al., "Trends in Cancer Incidence and Mortality," *IARC Scientific Publications*, 121:477-498 (1993).
Deyo, J. et al., "drp, A Novel Protein Expressed at High Cell Density But Not During Growth Arrest," *DNA and Cell Biol* 17:437-447 (1998).
Draghici, S., "The Constraint Based Decomposition," accepted for publication in *Neural Networks*, to appear (2001).
Einhorn, N. et al., "Prospective Evaluation of Serum CA 125 Levels for Early Detection of Ovarian Cancer," *Obstet Gynecol*, 80:14-18 (1992).
Golub, T.R. et al., "Molecular Classification of Cancer: Class Discovery and Class Prediction by Gene Expression Monitoring," *Science*, 286:531-537 (1999).
Gotlieb, W.H. et al., "Presence of Interleukins in the Ascites of Patients with Ovarian and other Intra-Abdominal Cancers," *Cytokine*, 4:385-390 (1992).
Greenlee, R.T. et al., "Cancer Statistics, 2000" *CA Cancer J Clin*, 50:7-33 (2000).
Heath, S. et al., "Induction of Oblique Decision Trees," Machine Learning, 1002-1007 (1993).
Hogdall, E.V. et al., "Predictive Values of Serum Tumour Markers Tetranectin, OVXI, CASA and CA125 in Patients with a Pelvic Mass," *Int J Cancer*, 89:519-523 (2000).

(Continued)

*Primary Examiner*—Lori A Clow
(74) *Attorney, Agent, or Firm*—Kohn & Associates PLLC

(57) ABSTRACT

There is provided a diagnostic tool for use in diagnosing diseases, the tool having a detector for detecting the presence of an array of markers indicative of disease. Also provided is a combination of markers for disease, the combination including at least two markers of the disease. A method of choosing such combinations of markers for a given disease as well as a method for detecting a combination of markers for diagnosing the presence of a disease state or determining a disease stage is also provided. The method includes selectively biopanning sera obtained from a patient to obtain cDNA clones to array for analysis and determining if the markers are present among the cDNA clones present in the disease. Epitopes found using this method are also provided as well as a database incorporating these epitopes. A biochip for detecting the presence of a disease marker in a patient's sera is provided, wherein the biochip has a detector contained within the biochip for detecting disease markers in a patient's sera.

1 Claim, 6 Drawing Sheets

OTHER PUBLICATIONS

Holschneider, C.H. et al., "Ovarian Cancer: Epidemiology, Biology, and Prognostic Factors," *Semin Surg Oncol*, 1:3-10 (2000).

Houts, T.M., "Improved 2-Color Normalization For Microarray Analyses Employing Cyanine Dyes," *CAMDA* (2000); "Critical Assessment of Techniques for Microarray Data Mining," Duke University Medical Center (2000).

Jacobs, I, et al., "The CA 125 Tumor-Associated Antigen: A Review of the Literature," *Hum Reprod*, 4:1-12 (1989).

Jacobs, I. et al., "Multimodal Approach to Screening For Ovarian Cancer," *Lancet*, I 268-271 (1988).

Jacobs, I J. et al., "Potential Screening Tests for Ovarian Cancer," *London, Chapman and Hall Medical*, 197-205 (1997).

Kacinski BM et al., "Macrophage Colony-Stimulating Factor is Produced by Human Ovarian and Endometrial Adenocarcinoma-Derived Cell Lines and is Present at Abnormally High Levels in the Plasma of Ovarian Carcinoma Patients with Active Disease," *Cancer Cells*, 7:333-337 (1989).

Kerr, Martin, Churchill, "Analysis of Variance for Gene Expression Microaaray Data," *Journal of Computational Biology* (2000).

Kim, Si Young et al., "Coordinate Control of Growth and Cytokeratin 13 Expression by Retinoic Acid," *Molecular Carcinogenesis*, 16:6-11 (1996).

Kohonen T., "Learning Vector Quantization," *Neural Networks*, 1 (suppl.1):303 (1988).

Lindstrom MS. et al., "p14ARF Homozygous Deletion or MDM2 Overexpression in Burkitt Lymphoma Lines Carrying Wild Tyoe p53," *Oncogene*. 20(17):2171-7 (2001).

MacBeath G. et al., "Printing Proteins as Microarrays for High-Throughout Function Determination," *Science*, 289:1760-3 (2000).

Murthy K., "On Growing Better Decision Trees From Data," Unpublished Doctoral Dissertation. John Hopkins University (1995).

Musavi M. et al., "On the Training of Radial Basis Function Classifiers," *Neural Networks* 5:595-603 (1992).

Nakashima M. et al. "Inhibition of Cell Growth and Induction of Apoptotic Cell Death By the Human Tumor-Associated Antigen RCAS1," *Nat Med*, 5:938-42 (1999).

Patsner B. et al., "Comparison of Serum CA 125 and Lipid Associated Sialic Acid (LASA-P) in Monitoring Patients with Invasive Ovarian Adenocarcinoma," *Gynecol Oncol*, 30(1): 98-103 (1988).

Peng YS. et al., "ARHI is the Center of Allelic Deletion on Chromosome 1p31 in Ovarian and Breast Cancers," *Int J Cancer*, 86:690-4 (2000).

Precup D. et al., "Classification Using Φ-Machines and Constructive Function Approximation," *In Proc*. 15th International Conf. On Machine Learning, 439-444 (1998).

Quinlan JR., "C4:5 Programs for Machine Learning," *Morgan-Kaufmann* (1993).

Rumelhart, DE. et al., "Learning Internal Representations by Error Backpropagation," *Parallel Distributed Processing: Explorations in the Microstructures of Cognition*, MIT Press/Bradford Books (1986).

Scmittgen TD. et al., "Quantitative Reverse Transcription-Polymerase Chain Reaction to Study mRNA Decay: Comparison of Endpoint and Real-Time Methods," *Anal Biochem*, 285:194-204 (2000).

Schwartz PE. et al., "Circulating Tumor Markers in the Monitoring of Gynecologic Malignacies," *Cancer* 60:353-361 (1987).

Sonoda K. et al., "A Novel Tumor-Associated Antigen Expressed in Human Uterine and Ovarian Carcinomas." *Cancer*, 77:1501-9 (1996).

\* cited by examiner

A

B

C

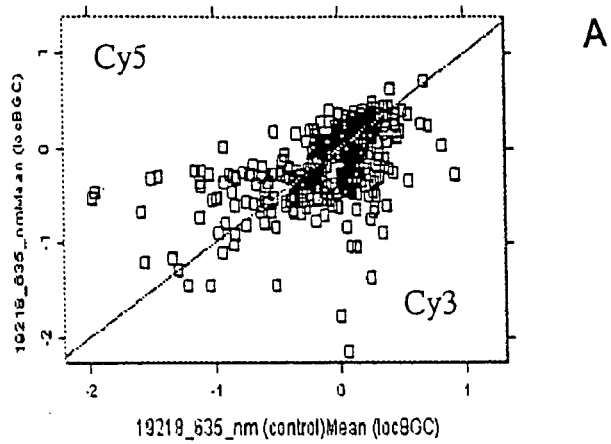
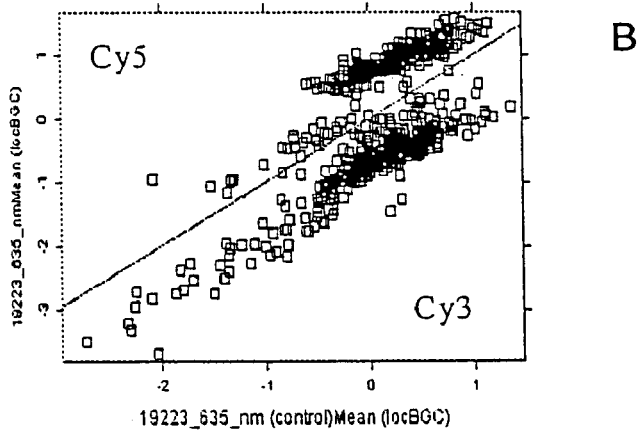
FIG. 9
FIG. 10

| Clones from patient | Source of sera | | | | | | | | | |
|---|---|---|---|---|---|---|---|---|---|---|
| | 1 | 2 | 3 | 4 | 5 | 6 | 7 | 8 | 9 | 10 |
| 2 | | 1 | | 1 | | | | 1 | | |
| 3 | | | 1 | | | 1 | | | | 1 |
| 5 | | | | | 1 | | | 1 | 1 | |
| 7 | | | | | | | 1 | | | 1 |
| 8 | | | | | | | | 1 | | |
| 9 | | | | | | | | | 1 | |
| 10 | | | | | | | | | | 1 |
| 1 | 1 | | | | | | | | | |
| 4 | | | | 1 | | | | | | |
| 6 | | | | | | 1 | | | | |
| | | | | | | | | | | |

FIG. 11

SEQUENCE LISTING

```
<160> NUMBER OF SEQ ID NOS: 2

<210> SEQ ID NO 1
<211> LENGTH: 20
<212> TYPE: DNA
<213> ORGANISM: ARTIFICIAL SEQUENCE
<220> FEATURE:
```

-continued

```
<223> OTHER INFORMATION: Artificially created primer
<220> FEATURE:
<221> NAME/KEY: misc_feature
<222> LOCATION: (1)..(20)
<223> OTHER INFORMATION: forward primer

<400> SEQUENCE: 1
tcttcgccca gaagctgcag                                                    20

<210> SEQ ID NO 2
<211> LENGTH: 22
<212> TYPE: DNA
<213> ORGANISM: ARTIFICIAL SEQUENCE
<220> FEATURE:
<223> OTHER INFORMATION: Artificially created primer
<220> FEATURE:
<221> NAME/KEY: misc_feature
<222> LOCATION: (1)..(22)
<223> OTHER INFORMATION: reverse primer

<400> SEQUENCE: 2
cctcctttca gcaaaaaacc cc                                                 22
```

NEOEPITOPE DETECTION OF DISEASE USING PROTEIN ARRAYS

BACKGROUND OF THE INVENTION

1. Technical Field

The present invention relates to an assay and method for diagnosing disease. More specifically, the present invention relates to an immunoassay for use in diagnosing cancer.

2. Background Art

It is commonly known in the art that genetic mutations can be used for detecting cancer. For example, the tumorigenic process leading to colorectal carcinoma formation involves multiple genetic alterations (Fearon et al (1990) Cell 61, 759-767). Tumor suppressor genes such as p53, DCC and APC are frequently inactivated in colorectal carcinomas, typically by a combination of genetic deletion of one allele and point mutation of the second allele (Baker et al (1989) Science 244, 217-221; Fearon et al (1990) Science 247, 49-56; Nishisho et al (1991) Science 253, 665-669; and Groden et al (1991) Cell 66, 589-600). Mutation of two mismatch repair genes which regulate genetic stability was associated with a form of familial colon cancer (Fishel et al (1993) Cell 75, 1027-1038; Leach et al (1993) Cell 75, 1215-1225; Papadopoulos et al (1994) Science 263, 1625-1629; and Bronner et al (1994) Nature 368, 258-261). Proto-oncogenes such as myc and ras are altered in colorectal carcinomas, with c-myc RNA being overexpressed in as many as 65% of carcinomas (Erisman et al (1985) Mol. Cell. Biol. 5, 1969-1976), and ras activation by point mutation occurring in as many as 50% of carcinomas (Bos et al (1987) Nature 327, 293-297; and Forrester et al (1987) Nature 327, 298-303). Other protooncogenes, such as myb and neu are activated with a much lower frequency (Alitalo et al (1984) Proc. Natl. Acad. Sci. USA 81, 4534-4538; and D'Emilia et al (1989) Oncogene 4, 1233-1239). No common series of genetic alterations is found in all colorectal tumors, suggesting that a variety of such combinations can be able to generate these tumors.

Increased tyrosine phosphorylation is a common element in signaling pathways which control cell proliferation. The deregulation of protein tyrosine kinases (PTKS) through overexpression or mutation has been recognized as an important step in cell transformation and tumorigenesis, and many oncogenes encode PTKs (Hunter (1989) in oncogenes and the Molecular Origins of Cancer, ed. Weinberg (Cold Spring Harbor Laboratory Press, Cold Spring Harbor, N.Y.), pp. 147-173). Numerous studies have addressed the involvement of PTKs in human tumorigenesis. Activated PTKs associated with colorectal carcinoma include c-neu (amplification), trk (rearrangement), and c-src and c-yes (mechanism unknown) (D'Emilia et al (1989), ibid; Martin-Zanca et al (1986) Nature 3, 743-748; Bolen et al (1987) Proc. Natl. Acad. Sci. USA 84, 2251-2255; Cartwright et al (1989) J. Clin. Invest. 83, 2025-2033; Cartwright et al (1990) Proc. Natl. Acad. Sci. USA 87, 558-562; Talamonti et al (1993) J. Clin. Invest. 91, 53-60; and Park et al (1993) Oncogene 8, 2627-2635).

Obviously, protein tyrosine phosphatases (PTPs) are also intimately involved in regulating cellular phosphotyrosine levels. The growing family of PTPs consists of non-receptor and receptor-like enzymes (for review see Charbonneau et al (1992) Annu. Rev. Cell. Biol. 8, 463-493; and Pot et al (1992) Biochim. Biophys. Acta 1136, 35-43). All share a conserved catalytic domain, which in the non-receptor PTPs is often associated with proximal or distal sequences containing regulatory elements directing protein-protein interaction, intracellular localization, or PTP stability. The receptor like PTPs usually contain two catalytic domains in their intracellular region, and in addition have a transmembrane region and heterogeneous extracellular regions. The extreme diversity of the extracellular region, compared to the relatively conserved intracellular portion of these enzymes, suggests that these PTPs are regulated by specific extracellular factors, few of which have been identified. Some PTPs can act in opposition to PTKS. For example, the nonreceptor PTP 1B and TC-PTP can reverse or block cell transformation induced by the oncogenic tyrosine kinases neu or v-fms, while another non-receptor PTP (known as 3HC134, CL100, HVH1, PAC-1, erp, or MKP-1) can reverse the PTK-mediated activation of a central signaling enzyme, MAP kinase (Brown-Shimer et al (1992) Cancer Res. 52, 478-482; Zander et al (1993) Oncogene 8, 1175-1182; Sun et al (1993) Cell 75, 487-493; and Ward et al (1994) Nature 367, 651-654). Conversely, other PTPs can act in conjunction with PTKs. Two receptor-like PTPs, PTPa and CD45, respectively activate the tyrosine kinases c-src or lck and fyn while the non-receptor SH-PTP2 (PTP 1D, PTP-2C, Syp) positively transduces a mitogenic signal from the PDGF receptor tyrosine kinase to ras (WP 94/01119; Zheng et al (1992) Nature 359, 336-339; den Hertog et al (1993) EMUB J. 12, 3789-3798; Mustelin et al (1989) Proc. Natl. Acad. Sci. USA 86, 6302-6306; Ostergaard et al (1989) Proc. Natl. Acad. Sci. USA 86, 8959-8963; Cahir McFarland et al (1989) Proc. Natl. Acad. Sci. USA 90, 1402-1406; and Li et al (1994) Mol. Cell. Biol. 14, 509-517).

Very few studies have examined alterations in PTP expression or activity that can be associated with tumorigenesis. As indicated above, two PTP-related mechanisms, either the inactivation or the overactivation of a PTP, could increase cellular phosphotyrosine levels and result in uncontrolled cell proliferation and tumorigenesis. In relation to PTP inactivation, it is of interest that the gene encoding receptor-like PTP7 is situated on a region of chromosome 3 that is often lost in renal and lung carcinomas, and that a PTPW allele is lost in some renal carcinoma and lung carcinoma cell lines (LaForgia et al (1991) Proc. Natl. Acad. Sci. USA 88, 5036-5040). As regards PTP overactivation, it has been shown that when PTPα is overexpressed in rat embryo fibroblasts, cell transformation occurs and the cells are tumorigenic in nude mice (WO 94/01119 and Zheng et al (1992), ibid). PTPa is a receptor-like enzyme with a short, unique extracellular domain and two tandem catalytic domains (WO 92/01050; Matthews et al (1990) Proc. Natl. Acad. Sci. USA 87, 4444-4448; Sap et al (1990) Proc. Natl. Acad. Sci. USA 87, 6112-6116; and Krueger et al (1990) EMBO J. 9, 3241-3252). Compared to many other receptor-like PTPs with a restricted and lineage-specific expression, PTPa is widely expressed (Sap et al (1990), ibid and Krueger et al (1990), ibid).

Mutations, such as those disclosed above can be useful in detecting cancer. However, there have been few advancements which can repeatably be used in diagnosing cancer prior to the existence of a tumor. For example, breast cancer which is by far the most common form of cancer in women is the second leading cause of cancer death in humans. Despite many recent advances in diagnosing and treating breast cancer, the prevalence of this disease has been steadily rising at a rate of about 1% per year since 1940. Today, the likelihood that a women living in North America can develop breast cancer during her lifetime is one in eight.

The current widespread use of mammography has resulted in improved detection of breast cancer. Nonetheless, the death rate due to breast cancer has remained unchanged at about 27 deaths per 100,000 women. All too often, breast cancer is discovered at a stage that is too far advanced, when therapeutic options and survival rates are severely limited. Accordingly, more sensitive and reliable methods are needed to detect small (less than 2 cm diameter), early stage, in situ carcinomas of the breast. Such methods should significantly improve breast cancer survival, as suggested by the successful employment of Papinicolou smears for early detection and treatment of cervical cancer.

In addition to the problem of early detection, there remain serious problems in distinguishing between malignant and benign breast disease, in staging known breast cancers, and in differentiating between different types of breast cancers (eg. estrogen dependent versus non-estrogen dependent tumors). Recent efforts to develop improved methods for breast cancer detection, staging and classification have focused on a promising array of so-called cancer "markers." Cancer markers are typically proteins that are uniquely expressed (eg. as a cell surface or secreted protein) by cancerous cells, or are expressed at measurably increased or decreased levels by cancerous cells compared to normal cells. Other cancer markers can include specific DNA or RNA sequences marking deleterious genetic changes or alterations in the patterns or levels of gene expression associated with particular forms of cancer.

A large number and variety of breast cancer markers have been identified to date, and many of these have been shown to have important value for determining prognostic and/or treatment-related variables. Prognostic variables are those variables that serve to predict disease outcome, such as the likelihood or timing of relapse or survival. Treatment-related variables predict the likelihood of success or failure of a given therapeutic plan. Certain breast cancer markers clearly serve both functions. For example, estrogen receptor levels are predictive of relapse and survival for breast cancer patients, independent of treatment, and are also predictive of responsiveness to endocrine therapy. Pertschuk et al., Cancer 66: 1663-1670, 1990; Parl and Posey, Hum. Pathol. 19: 960-966, 1988; Kinsel et al., Cancer Res. 49: 1052-1056, 1989; Anderson and Poulson Cancer 65: 1901-1908, 1989. Although breast cancer diagnosed at an early stage with positive expression of the estrogen receptor confers a good prognosis, approximately 30% of these women will suffer a relapse of their disease. Clearly more definitive biomarkers of prognosis are necessary.

The utility of specific breast cancer markers for screening and diagnosis, staging and classification, monitoring and/or therapy purposes depends on the nature and activity of the marker in question. For general reviews of breast cancer markers, see Porter-Jordan et al., Hematol. Oncol. Clin. North Amer. 8: 73-100, 1994; and Greiner, Pharmaceutical Tech., May, 1993, pp. 28-44. As reflected in these reviews, a primary focus for developing breast cancer markers has centered on the overlapping areas of tumorigenesis, tumor growth and cancer invasion. Tumorigenesis and tumor growth can be assessed using a variety of cell proliferation markers (for example Ki67, cyclin D1 and proliferating cell nuclear antigen (PCNA)), some of which can be important oncogenes as well. Tumor growth can also be evaluated using a variety of growth factor and hormone markers (for example estrogen, epidermal growth factor (EGF), erbB-2, transforming growth factor (TGF)a), which can be overexpressed, underexpressed or exhibit altered activity in cancer cells. By the same token, receptors of autocrine or exocrine growth factors and hormones (for example insulin growth factor (IGF) receptors, and EGF receptor) can also exhibit changes in expression or activity associated with tumor growth. Lastly, tumor growth is supported by angiogenesis involving the elaboration and growth of new blood vessels and the concomitant expression of angiogenic factors that can serve as markers for tumorigenesis and tumor growth.

In addition to tumorigenic, proliferation and growth markers, a number of markers have been identified that can serve as indicators of invasiveness and/or metastatic potential in a population of cancer cells. These markers generally reflect altered interactions between cancer cells and their surrounding microenvironment. For example, when cancer cells invade or metastasize, detectable changes can occur in the expression or activity of cell adhesion or motility factors, examples of which include the cancer markers Cathepsin D, plasminogen activators, collagenases and other factors. In addition, decreased expression or overexpression of several putative tumor "suppressor" genes (for example nm23, p53 and rb) has been directly associated with increased metastatic potential or deregulation of growth predictive of poor disease outcome.

In summary, the evaluation of proliferation markers, oncogenes, growth factors and growth factor receptors, angiogenic factors, proteases, adhesion factors and tumor suppressor genes, among other cancer markers, can provide important information concerning the risk, presence, status or future behavior of cancer in a patient. Determining the presence or level of expression or activity of one or more of these cancer markers can aid in the differential diagnosis of patients with uncertain clinical abnormalities, for example by distinguishing malignant from benign abnormalities. Furthermore, in patients presenting with established malignancy, cancer markers can be useful to predict the risk of future relapse, or the likelihood of response in a particular patient to a selected therapeutic course. Even more specific information can be obtained by analyzing highly specific cancer markers, or combinations of markers, which can predict responsiveness of a patient to specific drugs or treatment options.

Methods for detecting and measuring cancer markers have been recently revolutionized by the development of immunological assays, particularly by assays that utilize monoclonal antibody technology. Previously, many cancer markers could only be detected or measured using conventional biochemical assay methods, which generally require large test samples and are therefore unsuitable in most clinical applications. In contrast, modern immunoassay techniques can detect and measure cancer markers in relatively much smaller samples, particularly when monoclonal antibodies that specifically recognize a targeted marker protein are used. Accordingly, it is now routine to assay for the presence or absence, level, or activity of selected cancer markers by immunohistochemically staining tissue specimens obtained via conventional biopsy methods. Because of the highly sensitive nature of immunohistochemical staining, these methods have also been successfully employed to detect and measure cancer markers in smaller, needle biopsy specimens which require less invasive sample gathering procedures compared to conventional biopsy specimens. In addition, other immunological methods have been developed and are now well known in the art which allow for detection and measurement of cancer markers in non-cellular samples such as serum and other biological fluids from patients. The use of these alternative sample sources substantially reduces the morbidity and costs of assays compared to procedures employing conventional biopsy samples, which allows for application of cancer marker assays in early screening and low risk monitoring programs where invasive biopsy procedures are not indicated.

For the purpose of cancer evaluation, the use of conventional or needle biopsy samples for cancer marker assays is often undesirable, because a primary goal of such assays is to detect the cancer before it progresses to a palpable or detectable tumor stage. Prior to this stage, biopsies are generally contraindicated, making early screening and low risk monitoring procedures employing such samples untenable. Therefore, there is general need in the art to obtain samples for cancer marker assays by less invasive means than biopsy, for example by serum withdrawal.

Efforts to utilize serum samples for cancer marker assays have met with limited success, largely because the targeted markers are either not detectable in serum, or because telltale changes in the levels or activity of the markers cannot be monitored in serum. In addition, the presence of cancer markers in serum probably occurs at the time of micro-metastasis, making serum assays less useful for detecting pre-metastatic disease.

Previous attempts to develop non-invasive breast cancer marker assays utilizing mammary fluid samples have included studies of mammary fluid obtained from patients presenting with spontaneous nipple discharge. In one of these studies, conducted by Inaji et al., Cancer 60: 3008-3013, 1987, levels of the breast cancer marker carcinoembryonic antigen (CEA) were measured using conventional, enzyme linked immunoassay (ELISA) and sandwich-type, monoclonal immunoassay methods. These methods successfully and reproducibly demonstrated that CEA levels in spontaneously discharged mammary fluid provide a sensitive indicator of nonpalpable breast cancer. In a subsequent study, also by Inaji et al., Jpn. J. Clin. Oncol. 19: 373-379, 1989, these results were expanded using a more sensitive, dry chemistry, dot-immunobinding assay for CEA determination. This latter study reported that elevated CEA levels occurred in 43% of patients tested with palpable breast tumors, and in 73% of patients tested with nonpalpable breast tumors. CEA levels in the discharged mammary fluid were highly correlated with intratumoral CEA levels, indicating that the level of CEA expression by breast cancer cells is closely reflected in the mammary fluid CEA content. Based on these results, the authors concluded that immunoassays for CEA in spontaneously discharged mammary fluid are useful for screening nonpalpable breast cancer.

Although the evaluation of mammary fluid has been shown to be a useful method for screening nonpalpable breast cancer in women who experience spontaneous nipple discharge, the rarity of this condition renders the methods of Inaji et al, inapplicable to the majority of women who are candidates for early breast cancer screening. In addition, the first Inaji report cited above determined that certain patients suffering spontaneous nipple discharge secrete less than 10 .mu.l of mammary fluid, which is a critically low level for the ELISA and sandwich immunoassays employed in that study. It is likely that other antibodies used to assay other cancer markers can exhibit even lower sensitivity than the anti-CEA antibodies used by Inaji and coworkers, and can therefore not be adaptable or sensitive enough to be employed even in dry chemical immunoassays of small samples of spontaneously discharged mammary fluid.

In view of the above, an important need exists in the art for more widely applicable, non-invasive methods and materials to obtain biological samples for use in evaluating, diagnosing and managing breast and other diseases including cancer, particularly for screening early stage, nonpalpable tumors. A related need exists for methods and materials that utilize such readily obtained biological samples to evaluate, diagnose and manage disease, particularly by detecting or measuring selected cancer markers, or panels of cancer markers, to provide highly specific, cancer prognostic and/or treatment-related information, and to diagnose and manage pre-cancerous conditions, cancer susceptibility, bacterial and other infections, and other diseases.

With specific regard to such assays, specific antibodies can only be measured by detecting binding to their antigen or a mimic thereof. Although certain classes of immunoglobulins containing the antibodies of interest can, in some cases, be separated from the sample prior to the assay (Decker, et al., EP 0,168,689 A2), in all assays, at least some portion of the sample immunoglobulins are contacted with antigen. For example, in assays for specific IgM, a portion of the total IgM can be adsorbed to a surface and the sample removed prior to detection of the specific IgM by contacting with antigen. Binding is then measured by detection of the bound antibody, detection of the bound antigen or detection of the free antigen.

For detection of bound antibody, a labeled anti-human immunoglobulin or labeled antigen is normally allowed to bind antibodies that have been specifically adsorbed from the sample onto a surface coated with the antigen, Bolz, et al., U.S. Pat. No. 4,020,151. Excess reagent is washed away and the label that remains bound to the surface is detected. This is the procedure in the most frequently used assays, or example, for hepatitis and human immunodeficiency virus and for numerous immunohistochemical tests, Nakamura, et al., Arch Pathol Lab Med 112:869-877 (1988). Although this method is relatively sensitive, it is subject to interference from non-specific binding to the surface by non-specific immunoglobulins that can not be differentiated from the specific immunoglobulins.

Another method of detecting bound antibodies involves combining the sample and a competing labeled antibody, with a support-bound antigen, Schuurs, et al., U.S. Pat. No. 3,654,090. This method has its limitations because antibodies in sera binds numerous epitopes, making competition inefficient.

For detection of bound antigen, the antigen can be used in excess of the maximum amount of antibody that is present in the sample or in an amount that is less than the amount of antibody. For example, radioimmunoprecipitation ("RIP") assays for GAD autoantibodies have been developed and are currently in use, Atkinson, et al., Lancet 335:1357-1360 (1990). However, attempts to convert this assay to an enzyme linked immunosorbent assay ("ELISA") format have not been successful. The RIP assay is based on precipitation of immunoglobulins in human sera, and led to the development of a radioimmunoassay ("RIA") for GAD autoantibodies. In both the RIP and the RIA, the antigen is added in excess and the bound antigen:antibody complex is precipitated with protein A-Sepharose. The complex is then washed or further separated by electrophoresis and the antigen in the complex is detected.

Other precipitating agents can be used such as rheumatoid factor or C1q, Masson, et al., U.S. Pat. No. 4,062,935; polyethylene glycol, Soeldner, et al., U.S. Pat. No. 4,855,242; and protein A, Ito, et al., EP 0,410,893 A2. The precipitated antigen can be measured to indicate the amount of antibody in the sample; the amount of antigen remaining in solution can be measured; or both the precipitated antigen and the soluble antigen can be measured to correct for any labeled antigen that is non-specifically precipitated. These methods, while quite sensitive, are all difficult to carry out because of the need for rigorous separation of the free antigen from the bound complex, which requires at a minimum filtration or centrifugation and multiple washing of the precipitate.

Alternatively, detection of the bound antigen can be employed when the amount of antigen is less than the maximum amount of antibody. Normally, that is carried out using particles such as latex particles or erythrocytes that are coated with the antigen, Cambiaso, et al., U.S. Pat. No. 4,184,849 and Uchida, et al., EP 0,070,527 A1. Antibodies can specifically agglutinate these particles and can then be detected by light scattering or other methods. It is necessary in these assays to use a precise amount of antigen as too little antigen provides an assay response that is biphasic and high antibody titers can be read as negative, while too much antigen adversely affects the sensitivity. It is therefore necessary to carry out sequential dilutions of the sample to assure that positive samples are not missed. Further, these assays tend to detect only antibodies with relatively high affinities and the sensitivity of the method is compromised by the tendency for all of the binding sites of each antibody to bind to the antigen on the particle to which it first binds, leaving no sites for binding to the other particle.

For assays in which the free antigen is detected, the antigen can also be added in excess or in a limited amount although only the former has been reported. Assays of this type have been described where an excess of antigen is added to the sample, the immunoglobulins are precipitated, and the antigen remaining in the solution is measured, Masson, et al., supra and Soeldner, et al., supra. These assays are relatively insensitive because only a small percentage change in the amount of free antigen occurs with low amounts of antibody, and this small percentage is difficult to measure accurately.

Practical assays in which the free antigen is detected and the antigen is not present in excess of the maximum amount of antibody expected in a sample have not been described. However, in van Erp, et al., Journal of Immunoassay 12(3):425-443 (1991), a fixed concentration of monoclonal antibody was incubated with a concentration dilution series of antigen, and free antigen was then measured using a gold sol particle agglutination immunoassay to determine antibody affinity constants.

There has been much research in the area of evaluating useful markers for determining the risk factor for patients developing IDDM. These include insulin autoantibodies, Soeldner, et al., supra and circulating autoantibodies to glutamic acid decarboxylase ("GAD"), Atkinson, et al., PCT/US89/05570 and Tobin, et al., PCT/US91/06872. In addition, Rabin, et al., U.S. Pat. No. 5,200,318 describes numerous assay formats for the detection of GAD and pancreatic islet cell antigen autoantibodies. GAD autoantibodies are of particular diagnostic importance because they occur in preclinical stages of the disease, which can make therapeutic intervention possible. However, the use of GAD autoantibodies as a diagnostic marker has been impeded by the lack of a convenient, nonisotopic assay.

One assay method involves incubating a support-bound antigen with the sample, then adding a labeled anti-human immunoglobulin. This is the basis for numerous commercially available assay kits for antibodies such as the Syn elisa kit which assays for autoantibodies to $GAD^{65}$, and is described in product literature entitled "$Syn^{elisa}$ GAD II-Antibodies" (Elias USA, Inc.). Substantial dilution of the sample is required because the method is subject to high background signals from adsorption of non-specific human immunoglobulins to the support.

Many of the assays described above involve detection of antibody that becomes bound to an immobilized antigen. This can have an adverse affect on the sensitivity of the assay due to difficulty in distinguishing between specific immunoglobulins and other immunoglobulins in the sample, which bind non-specifically to the immobilized antigen. There is not only a need to develop an assay that avoids non-specific detection of immunoglobulins, but there is also the need for an improved method of detecting antibodies that combines the sensitivity advantage of immunoprecipitation assays with a simplified protocol. Finally, assays that can help evaluate the risk of developing diseases are medically and economically very important. The present invention addresses these needs.

SUMMARY OF THE INVENTION

According to the present invention, there is provided a diagnostic tool for use in diagnosing diseases, the tool including a detector for detecting the presence of an array of markers indicative of disease. Also provided is a combination of markers for disease, the combination including at least two markers of the disease. A method of detecting a combination of markers for diagnosing the presence of a disease state or determining a disease stage is also provided. The method includes selectively biopanning sera obtained from a patient to obtain cDNA clones to array for analysis and determining if the markers are present among the cDNA clones present in the disease. The method also includes using data analysis tools necessary to select the most informative epitopes as well as using data analysis tools to interpret the results of a test performed with such technology. Epitopes found using this method are also provided as well as a database incorporating these epitopes. A biochip for detecting the presence of the disease state in a patient's sera is provided, wherein the biochip has a detector contained within the biochip for detecting microbes in a patient's sera.

DESCRIPTION OF THE DRAWINGS

Other advantages of the present invention are readily appreciated as the same becomes better understood by reference to the following detailed description when considered in connection with the accompanying drawings wherein:

FIG. 6A is a photograph showing the comparison of serum reaction of control and breast cancer patient with phagotopes from BP4; and FIG. 6B is a graph of the BP4 filters which were scanned thereby showing the ratio of the pixel densities plotted in rank order; FIG. 6C is a scan of a microarray demonstrating the binding a Cy5-labeled antihuman IgG to human IgG from patient #1's serum and the control Cy3-labeled antibody to phage T7 capsid protein to phage clones microarrayed on glass;

FIG. 9 shows a comparison between the scatterplot of a control subject (19218) with a strong but non-specific reaction and the scatterplot of a patient MEC1 (19223), the scattergrams plot the background corrected mean intensity of the human IgG labeled with Cy5 vs. the background corrected mean intensity of the T7 labeled with Cy3;

FIG. 10 shows the matrix of reactivity between sets of clones coming from patients 1-12 (in rows) and sera from same patients (in columns), at this point (step 2 of Procedure 2), the matrix contains the results of the self-reactions: patients 1-10 have a specific self-reaction whereas patients 11 and 12 do not, Patients 11 and 12 are eliminated from the clone selection procedure; and FIG. 11 shows a matrix of reactivity between sources of clones and different sera ordered by reactivity; the clones from patient 2 react with sera from self (column 2) and patients 4 and 8; the clones from patient 3 react with sera from self (column 3) and patients 6 and 10, etc, note that the union of the set of clones coming from patients 2, 3, 5, 7 and 1 will ensure that the chip made with these clones reacts with all patients.

DETAILED DESCRIPTION OF THE INVENTION

Figure 1:
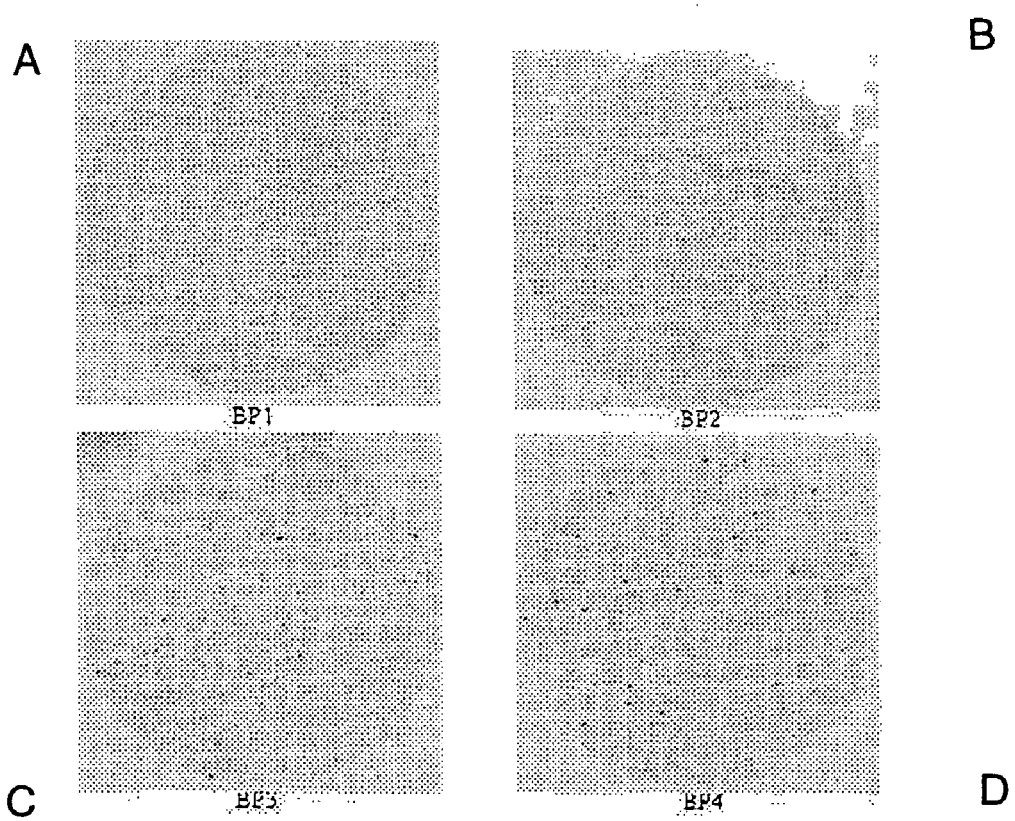
FIGS. 1A-D are photographs showing the identification of a phage displaying peptide sequence of Sirt2 by plaque lift.

Generally, the present invention provides a method and combination of markers for use in detecting disease and stages of disease. In other words, the markers are able to be used to determine the presence of disease without requiring the presence of symptoms.

The method and combination of markers of the present invention can be used to diagnose the presence of a disease or a disease stage in a patient. The method of the present invention utilizes a detector device for detecting the presence of an array or combination of markers in the serum of the patient.

The detector includes, but is not limited to an assay, a slide, a filter, computer software implementing the data analysis methods, and any combinations thereof. The detector can also include a two-color detection system or other detector system known to those of skill in the art.

By "biopanning", it is meant a selection process for use in screening a library (Parmley and Smith, Gene, 73:308 (1988); Noren, C. J., NEB Transcript, 8(1);1(1996)). Biopanning is carried out by incubating phages encoding the peptides with a plate coated with the proteins, washing away the unbound phage, eluting, and amplifying the specifically bound phage. Those skilled in the art readily recognize other immobilization schemes which can provide equivalent technology, such as but not limited to binding the proteins or other targets to beads.

By staging the disease, as for example in cancer, it is intended to include determining the extent of a cancer, especially whether the disease has spread from the original site to other parts of the body. The stages can range from 0 to 5 with 0 being the presence of cancerous cells and 5 being the spread of the cancer cells to other parts of the body including the lymph nodes.

The term "marker" as used herein is intended to include, but is not limited to, a gene or a piece of a gene which codes for a protein, a protein such as a fusion protein, open reading frames such as ESTs, epitopes, mimitopes, and any other indicator of immune response. A combination of markers, or an array, is used in order to better analyze the sera of the patient. This array or combination is at least two markers which can be used to diagnose or stage a disease.

The present invention further includes a random peptide epitope (mimitope) that mimics a natural antigenic epitope during epitope presentation. Such mimitopes are useful in the applications and methods discussed above. Also included in the present invention is a method of identifying a random peptide epitope. In the method, a library of random peptide epitopes is generated or selected. The library is contacted with an anti-antibody. Mimitopes are identified that are specifically immunoreactive with the antibody. Sera (containing anti antibodies) or antibodies generated by the methods of the present invention can be used. Random peptide libraries can, for example, be displayed on phage or generated as combinatorial libraries.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the various immunoglobulin diversity/joining/variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$—$C_H1$ by a disulfide bond. The $F(ab)'_2$ can be reduced under mild conditions to break the disulfide linkage in the hinge region, thereby converting the $F(ab)'_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill can appreciate that such fragments can be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy (1985)). Techniques for the production of single chain antibodies (U.S. Pat. No. 4,946,778) can be adapted to produce antibodies to polypeptides of this invention. Also, transgenic mice, or other organisms such as other mammals, can be used to express humanized antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay wherein an antibody specifically binds to an antigen. The immunoassay is characterized by the use of specific binding properties of a particular antibody to isolate, target, and/or quantify the antigen. In addition, an antigen can be used to capture or specifically bind an antibody.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions can require an antibody that is selected for its specificity for a particular protein. For example, polyclonal antibodies raised to modified .beta.-tubulin from specific species such as rat, mouse, or human can be selected to obtain only those polyclonal antibodies that are specifically immunoreactive, e.g., with .beta.-tubulin modified at cysteine 239 and not with other proteins. This selection can be achieved by subtracting out antibodies that cross-react with other molecules. Monoclonal antibodies raised against modified .beta.-tubulin can also be used. A variety of immunoassay formats can be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction can be at least twice background signal or noise and more typically more than 10 to 100 times background.

A "label" or a "detectable moiety" is a composition detectable by spectroscopic, photochemical, biochemical, immunochemical, or chemical means. For example, useful labels include $^{32}P$, fluorescent dyes, iodine, electron-dense reagents, enzymes (e.g., as commonly used in an ELISA), biotin, digoxigenin, or haptens and proteins for which antisera or monoclonal antibodies are available, e.g., by incorporating a radiolabel into the peptide.

A "labeled antibody or probe" is one that is bound, either covalently, through a linker or a chemical bond, or noncovalently, through ionic, van der Waals, electrostatic, or hydrogen bonds to a label such that the presence of the antibody or probe can be detected by detecting the presence of the label bound to the antibody or probe.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

By "support or surface" as used herein, the term is intended to include, but is not limited to a solid phase which is typically a support or surface, which is a porous or non-porous water insoluble material that can have any one of a number of shapes, such as strip, rod, particle, including beads and the like. Suitable materials are well known in the art and are described in, for example, Ullman, et al. U.S. Pat. No. 5,185, 243, columns 10-11, Kurn, et al., U.S. Pat. No. 4,868,104, column 6, lines 21-42 and Milburn, et al., U.S. Pat. No. 4,959,303, column 6, lines 14-31 which are incorporated herein by reference. Binding of ligands and receptors to the support or surface can be accomplished by well-known techniques, readily available in the literature. See, for example, "Immobilized Enzymes", Ichiro Chibata, Halsted Press, New York (1978) and Cuatrecasas, J. Biol. Chem. 245:3059 (1970). Whatever type of solid support is used, it must be treated so as to have bound to its surface either a receptor or ligand that directly or indirectly binds the antigen. Typical receptors include antibodies, intrinsic factor, specifically reactive chemical agents such as sulfhydryl groups that can react with a group on the antigen, and the like. For example, avidin or streptavidin can be covalently bound to spherical glass beads of 0.5-1.5 mm and used to capture a biotinylated antigen.

Signal producing system ("sps"): one or more components, at least one component being a label, which generate a detectable signal that relates to the amount of bound and/or unbound label, i.e. the amount of label bound or not bound to the compound being detected. The label is any molecule that produces or can be induced to produce a signal, such as a fluorescer, enzyme, chemiluminescer or photosensitizer. Thus, the signal is detected and/or measured by detecting enzyme activity, luminescence or light absorbance.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as Q-beta replicase; promoters; dyes; fluorescers such as fluorescein, isothiocyanate, rhodamine compounds, phycoerythrin, phycocyanin, allophycocyanin, o-phthaldehyde, and fluorescamine; chemiluminescers such as isoluminol; sensitizers; coenzymes; enzyme substrates; photosensitizers; particles such as latex or carbon particles; suspendable particles; metal sol; crystallite; liposomes; cells, etc., which can be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference. Preferably, at least one sps member is selected from the group consisting of fluorescers, enzymes, chemiluminescers, photosensitizers and suspendable particles.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the sps can then include all the components required to produce a measurable signal, which can include substrates, coenzymes, enhancers, additional enzymes, substances that react with enzymatic products, catalysts, activators, cofactors, inhibitors, scavengers, metal ions, specific binding substance required for binding of signal generating substances, and the like. A detailed discussion of suitable signal producing systems can be found in Ullman, et al. U.S. Pat. No. 5,185,243, columns 11-13, which is incorporated herein by reference.

The label is bound to a specific binding pair (hereinafter "sbp") member which is the antigen, or is capable of directly or indirectly binding the antigen, or is a receptor for the antigen, and includes, without limitation, the antigen; a ligand for a receptor bound to the antigen; a receptor for a ligand bound to the antigen; an antibody that binds the antigen; a receptor for an antibody that binds the antigen; a receptor for a molecule conjugated to an antibody to the antigen; an antigen surrogate capable of binding a receptor for the antigen; a ligand that binds the antigen, etc. Binding of the label to the sbp member can be accomplished by means of non-covalent bonding as for example by formation of a complex of the label with an antibody to the label or by means of covalent bonding as for example by chemical reactions which result in replacing a hydrogen atom of the label with a bond to the sbp member or can include a linking group between the label and the sbp member. Such methods of conjugation are well known in the art. See for example, Rubenstein, et al., U.S. Pat. No. 3,817,837, which is incorporated herein by reference. Other sps members can also be bound covalently to sbp members. For example, in Ullman, et al., U.S. Pat. No. 3,996,345, two sps members such as a fluorescer and quencher can be bound respectively to two sbp members that both bind the analyte, thus forming a fluorescer-sbp$_1$:analyte:sbp$_2$-quencher complex. Formation of the complex brings the fluorescer and quencher in close proximity, thus permitting the quencher to interact with the fluorescer to produce a signal. This is a fluorescent excitation transfer immunoassay. Another concept is described in Ullman, et al., EP 0,515,194 A2, which uses a chemiluminescent compound and a photosensitizer as the sps members. This is referred to as a luminescent Oxygen channeling immunoassay. Both the aforementioned references are incorporated herein by reference.

The analysis of mRNA expression in tumors does not necessarily reveal the status of protein levels in the cancer cells. Other factors such as protein half-life and mutation can be altered without an effect on mRNA levels thus masking significant molecular changes at the protein level. Serum antibody reactivity to cellular proteins occurs in cancer patients due to presentation of mutated forms of proteins from the tumor cells or overexpression of proteins in the tumor cells. Thus the host immune system can direct individuals to molecular events critical to the genesis of the disease. Using a candidate gene approach, experience has shown that the frequency of serum positivity to any single protein is low. Therefore to increase the identification of such autoantigens, a more global approach is employed to exploit immunoreactivity to identify large numbers of cDNAs coding for proteins that are mutated or upregulated in cancer cells.

In order to develop an effective screening test for early detection of ovarian cancer, cDNA phage display libraries are used to isolate cDNAs coding for epitopes reacting with antibodies present specifically in the sera of patients with ovarian cancer. The methods of the present invention detect various antibodies that are produced by patients in reaction to proteins expressed in their ovarian tumors. This is achievable by differential biopanning technology using human sera collected both from normal individuals and patients having ovarian cancer and phage display libraries expressing cDNAs of genes expressed in ovarian epithelial tumors and cell lines. Serum reactivity toward a cellular protein can occur because of the presentation to the immune system of a mutated form of the protein from the tumor cells or overexpression of the protein in the tumor cells. The strategy provides for the identification of epitope-bearing phage clones (phagotopes) displaying reactivity with antibodies present in sera of patients having ovarian cancer but not in control sera from unaffected women. This strategy leads to the identification of novel disease-related epitopes for diseases including, but not limited to ovarian cancer, that have prognostic/diagnostic value with additional potential for therapeutic vaccines and medical imaging reagents. This also creates a database which can be used to determine both the presence of disease and the stage of the disease.

The series of experiments disclosed herein provide direct evidence that biopanning a T7 coat protein fusion library can isolate epitopes for antibodies present in polyclonal sera. This also showed that the technology can be applied to direct microarray screening of large numbers of selected phage against numerous patient and control sera. This approach provides a large number of biomarkers for early detection of disease.

More specifically, the methods of the present invention provide four to five cycles of affinity selection and biopanning which are carried out with biological amplification of the phage after each biopanning, meaning growth of the biological vector of the cDNA expression clone in a biological host. Examples of biological amplification include but are not limited to growth of a lytic or lysogenic bacteriophage in host bacteria or transformation of bacterial host with selected DNA of the cDNA expression vector. The number of biopanning cycles generally determines the extent of the enrichment for phage that binds to the sera of patient with ovarian cancer. This strategy allows for one cycle of biopanning to be performed in a single day. Someone skilled in the art can establish different schedules of biopanning which provide the same essential features of the procedure described above.

Two biopanning experiments are performed with each library differentially selecting clones between control and disease patient sera. The first selection is to isolate phagotope clones that do not bind to control sera pooled from control women but do bind to a pool of disease patient serum. This set of phagotope clones represent epitopes that are indicative of the presence of disease as recognized by the host immune system. The second type of screening is performed to isolate phagotope clones that did not bind to a pool of control sera but do bind to an individual patient's serum. Those sets of phagotope clones represent epitopes that are indicative of the presence of disease.

Subsequent to the biopanning, the clones so isolated can be used to contact antibodies in sera by spotting the clones or peptide sequences of amino acids containing those encoded by the clones. After spotting on a solid support, the arrays are rinsed briefly in a 1% BSA/PBS to remove unbound phage, then transferred immediately to a 1% BSA/PBS blocking solution and allowed to sit for 1 hour at room temperature. The excess BSA is rinsed off from the slides using PBS. This step insures that the elution step of antibodies is more effective. The use of PBS elutes all of the antibodies without harming the binding of the antibody. Antibody detection of reaction with the clones or peptides on the array is carried out by labeling of the serum antibodies or the use of a labeled secondary antibody which reacts with the patient's antibodies. A second control reaction to every spot allows for greater accuracy of the quantitation of reactivity and increases sensitivity of detection.

The slides are subsequently processed to quantify the reaction of each phagotopes. Such processing is specific to the label used. For instance, if fluorophore cy3-cy5 labels are used, this processing is done in a laser scanner that captures an image of the slide for each fluorophore used. Subsequent image processing familiar to those skilled in the art can provide intensity values for each phagotope.

The data analysis can be divided into the following steps:
1. Pre-processing and normalization.
2. Identifying the most informative markers
3. Building a predictor for molecular diagnosis of ovarian cancer and validating the results.

The purpose of the first step is to cleanse the data from artifacts and prepare it for the subsequent steps. Such artifacts are usually introduced in the laboratory and include: slide contamination, differential dye incorporation, scanning and image processing problems (e.g. different average intensities from one slide to another), imperfect spots due to imperfect arraying, washing, drying, etc. The purpose of the second step is to select the most informative phages that can be used for diagnostic purposes. The purpose of the third step is to develop a software classifier able to diagnose cancer based on the antibody reactivity values of the selected phages. The last step also includes the validation of this classifier and the assessment of its performance using various measures such as specificity, sensitivity, positive predictive value and negative predictive value. The computation of such measures can be done on cases not used during the design of the chip in order to assess the real-world performance of the diagnosis tool obtained.

The pre-processing and normalization step is used for arrays using two channels such as Cy5 for the human IgG and Cy3 for the T7 control, the spots are segmented and the mean intensity is calculated for each spot. A mean intensity value is calculated for the background, as well. A background corrected value is calculated by subtracting the background from the signal. If necessary, non-linear dye effects can be eliminated by performing an exponential normalization (Houts, 2000) and/or LOESS normalization of the data and/or a piecewise linear normalization (see FIGS. 7A-D). The values coming from each channel are subsequently divided by their mean of the intensities over the whole array. Subsequently, the ratio between the IgG and the T7 channels was calculated. The values coming from replicate spots (spots printed in quadruplicates) are combined by calculating mean and standard deviation. Outliers (outside+/−two standard deviations) are flagged for manual inspection). Single channel arrays are pre-processed in a similar way but without taking the ratios. This preprocessing sequence was shown to provide good results for all preliminary data analyzed.

The step of selecting the most informative markers is used to identify the most informative phages out of the large set of phages started with. The better the selection, the better is the expected accuracy of the diagnosis tool.

A first test is necessary to determine whether a specific epitope is suitable for inclusion in the final set to be spotted. The selection methods to be applied follow the principles of the methods successfully applied in (Golub et al., 1999; Alizadeh et al., 2000) and can be briefly described in the following.

Procedure 1

Figure 8:
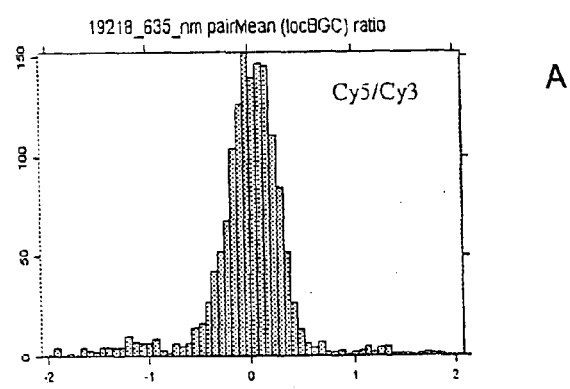
FIG. 8 shows an example comparison between the histogram of a control subject (19218) with a high but non-specific reaction to the left, and the histogram of a patient (19223), to the right; the histograms are calculated on the ratios of the background corrected mean intensity of the human IgG labeled with Cy5 vs. the background corrected mean intensity of the T7 labeled with Cy3.
Figure 8:
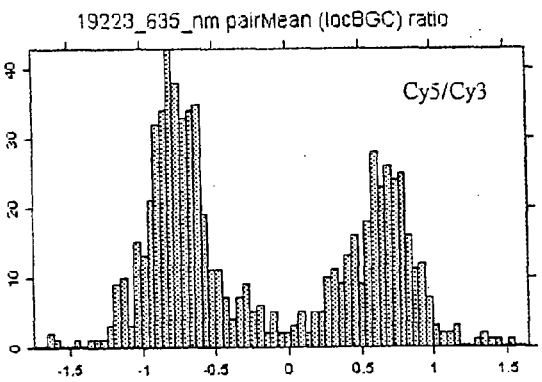

This is started by defining a template for the cancer case (FIG. 8). Unlike gene expression experiments where the expression level of a gene can be either up or down in cancer vs. healthy subjects, here one is testing for the presence of antibodies specific to cancer were tested for. Therefore, epitopes with high reactivity in controls and low reactivity in patients are not expected and the profile to the left in FIG. 8 is sufficient. Each epitope can have a profile across the given set of patients (FIGS. 9A and B). The profile of each epitope is compared with the templates using a correlation-based distance. Those skilled in the art will recognize that the other distances may be used without essentially changing the procedure.

Figure 7:
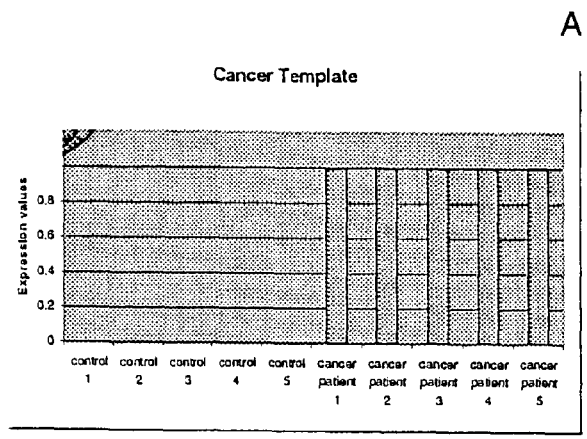
FIG. 7 shows the method of finding informative epitopes: The spot intensities are plotted on the vertical axis for 12 subjects (controls to the left and patients to the right) the template defined on the left (shown in blue) was used with a correlation distance, a correlation threshold of 0.8 selected the 46 epitopes shown here in red (out of the total of 4×96=384 shown here in yellow)
Figure 7:
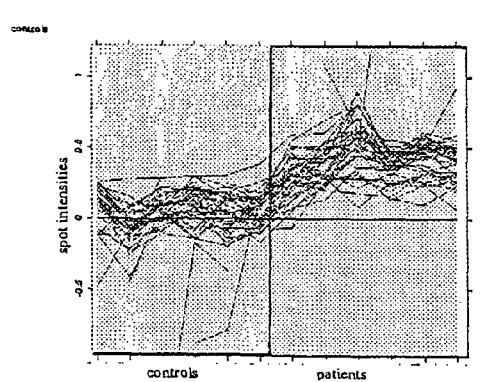

The epitopes are then ordered based on the similarity between the reference profile (FIG. 8) and their actual profile. FIG. 7 shows 46 epitopes found informative for a correlation threshold of 0.8. The final cutoff threshold is calculated by doing 1000 random permutations once the whole data set become available. Each such permutation moves randomly the subjects between the 'patient' and 'control' categories. Calculating the score of each epitope profile for such permutations allows us to establish a suitable threshold for the similarity (Golub et. al. 1999).

The technique follows closely the one used in (Golub, 1999). However, the technique can be further improved as follows. Firstly, this technique was shown to provide good results if most controls are consistent by providing the same type of reactivity. However, preliminary data showed that there are control subjects that show a non-specific reactivity with all clones (see FIG. 1b). While still clearly different from patients. FIG. 8 shows a comparison between the histogram profile of a control subject showing a non-specific reaction (19218) with and the profile of a patient (19223). FIG. 9 shows the scatterplots of the same subjects. While still clearly different from patients, such control subjects with a high non-specific reaction introduces spikes in the clone profile in the area corresponding to the control subjects (right left hand side of the template in FIG. 8). Such spikes decrease the score of the relevant clones making them more difficult to distinguish from the irrelevant ones. In order to reduce this effect, all control subjects with a non-specific response (i.e a unimodal distribution such as in the left panel of FIG. 7) were eliminated from the analysis leading to the epitope selection.

A second essential modification is related to the set of epitopes selected. There are rare patients who might react only to a small number of very specific epitopes. If the selection of the epitopes is done on statistical grounds alone, such very specific epitopes can be missed if the set of patients available contains only few such rare patients. In order to maximize the sensitivity of the penultimate test resulted from this work, every effort was made to include epitopes which might be the only ones reacting to rare patients. In order to do this, the information content of the set of epitopes is maximized while trying to minimize the number of epitopes used using the following procedure.

Procedure 2

Assume there are m patients and k controls. Select n random patients from the m available. For each of the n patients used for epitope selection, amplify (n×4 biopannings) and do self reactions. Eliminate those patients/epitopes that do not react to self.

Make a chip with all available, self-reacting epitopes printed in quadruplicates. React this chip with all patients and controls (n+k antibody reactions). Eliminate controls with a non-specific reactivity. For the set of epitopes coming from a single patient, apply Procedure 1 to order the epitopes in the order of their informational content and select the ones that can be used to differentiate patients from controls.

Order the epitopes by their reactivity in decreasing order of the number of patients they react to. Scan this list from the top down, moving epitopes from this list to the final set. Every time a set of epitopes coming from a patient x is added to the final set, the patient x and all other patients that these epitopes react to are represented in the current set of epitopes. Repeat until all patients are represented in the current set of epitopes.

This procedure tries to minimize the number of epitopes used while maximizing the number of patients that react to the chip containing the selected epitopes.

The following example shows how this procedure works using a simple example. The matrix in FIG. 10 contains a row i for the clones coming from patient i and a column j for the serum coming from patient j. A serum is said to react specifically with a set of clones if the histogram of the ratios is bimodal (see subject 19218 in FIGS. 8 and 9). A serum is said to react non-specifically if the histogram of the ratio is unimodal (see subject 19223 in FIGS. 8 and 9). Furthermore, a serum might not react at all with a set of clones. If the serum from patient j reacts specifically with the clones from patient i, the matrix can contain a value of 1 at the position (i, j). The element at position (i, j) is left blank if the there is no reaction or the reaction is non-specific.

Each set of epitopes corresponding to a row of the matrix is pruned by sub-selecting epitopes according to Procedure 1. The rows are now sorted in decreasing reactivity (number of patients other than self that the clones react to). For instance, in FIG. 11, the clones from patient 2 react with sera from self (column 2) and patients 4 and 8. The clones from patient 3 react with sera from self (column 3) and patients 6 and 10, etc. The final set of clones were obtained from patients 2, 3, 5, 7 and 1 (reading top-down in column 1). Clones coming from patients 8, 9 and 10 are not included since these patients already react to clones coming from other patients. This set ensures that the chip made with these clones reacts with all patients in this example.

Procedure 3

Arrays using two channels such as Cy5 for the human IgG and Cy3 for the T7 control are processed as follows. The spots are segmented and the mean intensity is calculated for each spot. A mean intensity value is calculated for the background, as well. A background corrected value is calculated by subtracting the background from the signal. The values coming from each channel are normalized by dividing by their mean. Subsequently, the ratio between the IgG and the T7 channels are calculated and a logarithmic function is applied. The values coming from replicate spots (spots printed in quadruplicates) are combined by calculating mean and standard deviation. Outliers (outside+/−two standard deviations) are flagged for manual inspection. Someone skilled in the art can recognize that various combinations and permutations of the steps above or similar could replace the normalization procedure above without substantially changing rest of the data analysis process. Such similar steps include without limitation taking the median instead of the mean, using logarithmic functions in various bases, etc.

The histogram of the average log ratio is calculated. If the histogram is unimodal (e.g subject 19223 in FIG. 7), there is no specific response. If the histogram is clearly bimodal (e.g. subject 19218 in FIG. 7), there is a specific response. All 25 subjects analyzed so far fell in one of these two categories or had no response at all. A mixed probability model is used in less clear cases to fit two normal distributions as in (Lee, 2000). If the two distributions found under the maximum likelihood assumption are separated by a distance d of more than 2 standard deviations (corresponding to a p-value of approximately 0.05), there is a specific response. If the distance is less than 2 standard deviations, the response can be considered as not specific. The preliminary data analyzed so far showed a very good separation of the distributions for the patients.

Once the chosen clones are spotted on the final version of the array, a number of sera coming from both patients and controls can be tested. These sera come from subjects not used in any of the phases that lead to the fabrication of the array (i.e. not involved in clone selection, not used as controls, etc.). Each test was evaluated using Procedure 3 above. The performance on this validation data can be reported in terms of PPV, NPV, specificity and sensitivity. Since these performance indicators are calculated on data not previously used, they provide a good indication of the performance of the test for screening purposes for the various categories of patients envisage in the general population.

The present invention also provides a kit including all of the technology for performing the above analysis. This is included in a container of a size sufficient to hold all of the required pieces for analyzing sera, as well as a digital medium such as a floppy disk or CDROM containing the software necessary to interpret the results of the analysis. These components include the array of clones or peptides spotted onto a solid support, prewashing buffers, a detection reagent for identifying reactivity of the patients' serum antibodies to the spotted clones or peptides, post-reaction washing buffers, primary and secondary antibodies to quantify reactivity of the patients serum antibodies with the spotted array and methods to analyze the reactivity so as to establish an interpretation of the serum reactivity.

A biochip for detecting the presence of the disease state in a patient's sera is provided by the present invention. The biochip has a detector contained within the biochip for detecting antibodies in a patient's sera. This allows a patient's sera to be tested for the presence of a multitude of diseases or reaction to disease markers using a single sample and the analysis can be conducted and analyzed on a single chip. By utilizing such a chip this lowers the time required for the detection of disease while also enabling a doctor to determine the level of disease spread or infection.

The above discussion provides a factual basis for the use of the combination of markers and method of making the combination. The methods used with a utility of the present invention can be shown by the following non-limiting examples and accompanying figures.

EXAMPLES

Example 1 mRNA from one ovarian cancer cell line, SKOV3 and ovarian tumor tissues, was copied into cDNA and libraries prepared. Tumor tissue in excess of that needed for pathological evaluation was obtained by informed consent from ovarian cancer patients.

Sera was obtained from 1) ovarian cancer patients at the time of diagnosis and at six month intervals during the follow up physician visits; 2) unaffected women for control sera.

T7 cDNA phage display expression libraries are prepared for biopanning experiments, to select phage bearing epitopes ie phagotopes that are recognized by sera from women with ovarian cancer but not recognized by normal sera from unaffected women. For the biopanning process, sera from women in the control group was pooled to avoid individual variations unrelated to the presence of ovarian cancer.

The selection of the most informative epitopes was done by comparing the immune reaction profile of each individual epitope with templates defined for each disease stage. Several distances and information entropy measures were used. Several predictors were constructed based on three selected machine learning techniques using only a part of the available data. Specificity, sensitivity, positive predicted value and negative predicted value were calculated for each such classifier. The validation of the predictors and the selection of the best predictor was done by cross-validation on cases that have not been used during the predictor construction.

For example, to develop an effective screening test for early detection of ovarian cancer, cDNA phage display libraries were used to isolate cDNAs coding for epitopes reacting with antibodies present in the sera of patients with ovarian cancer. Screening of T7 phage cDNA library with serum containing polyclonal antibodies against a known protein, leads to the enrichment of one particular phage clone (which displays the peptide sequence recognized by the antibody on its coat) after several rounds of biopanning. Serum containing polyclonal antibodies were raised against a C-terminal 12 amino acid peptide from the human homologue of the yeast SIRT2 protein and screened against a T7 phage human brain cDNA library. This library was used because the Sirt2 transcript is expressed in human brain. Preimmune rabbit serum was bound to protein-G agarose beads and $6 \times 10^{10}$ phage were added to the beads. The unbound phage were then bound to protein-G agarose beads to which the Sirt2p antibody was previously bound. The nonspecifically bound phage were washed away with PBS and the specifically bound phage eluted with 1% SDS. T7 phage is stable in this solution. These phage are diluted to reduce the SDS concentration and used to infect bacteria for amplification and another cycle of biopanning. Table 1 shows the value of the titer of the T7 phage library after each cycle of biopanning. This table reveals that the titer of the eluate after each round of biopanning increased with each successive cycle of antibody selection.

E. coli BLT5615 infected with amplified phage library after biopanning 1-4 were plated onto LB-Agar plates and plaque lifts were performed for all the individual plates. The plaque lift filter membranes were then hybridized with a $P^{32}$-labeled Sirt2 cDNA probe. The percentage of positive plaques (number of positive plaques/total number of plaques×100) as determined for each plates labeled BP1-4, FIG. 1 increased with each successive cycle of biopanning. For BP1 and BP2 the percentage of positive plaques was negligible. For BP3 and BP4, percentage of positive plaques was 1.7% and 8.6% respectively.

Figure 2:
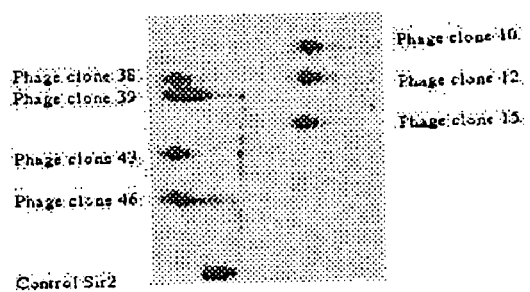
FIG. 2 is a photograph showing the analysis of the PCR product of the plaques by Southern Blot hybridization.
Figure 3:
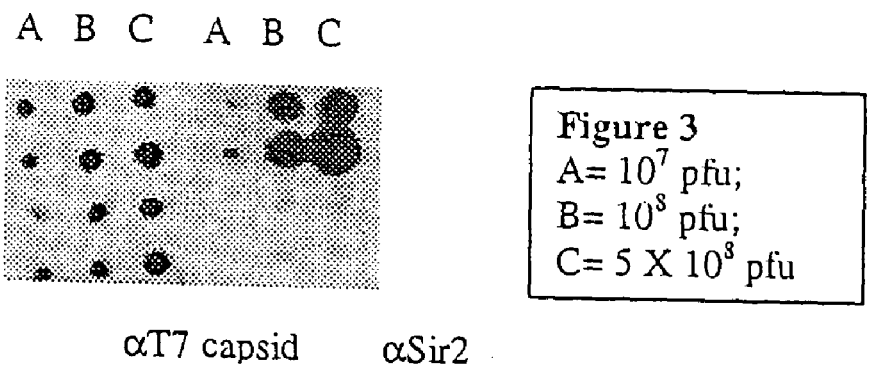
FIG. 3 is a photograph showing the Dot Blot analysis of Sirt2 positive plaques.
Figure 4:
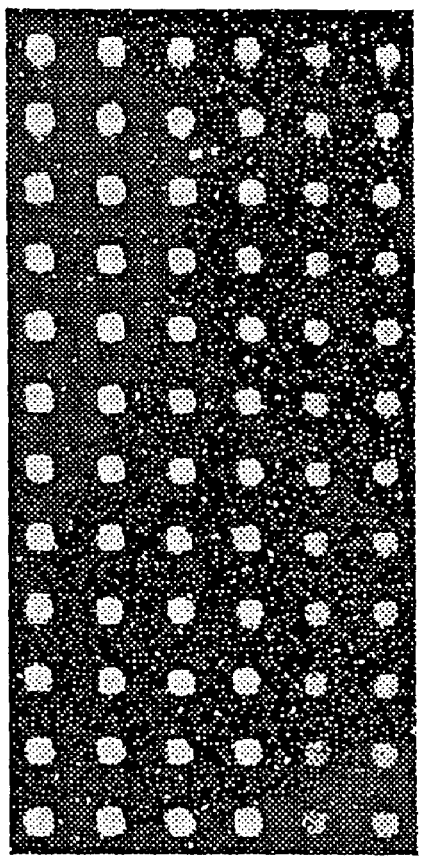
FIG. 4 is a photograph showing green and red labeled detection of serum antibodies indicative of the antibody reaction to the protein.

In order to confirm that those positive plaques contain phage clones displaying the peptide sequence of Sirt2, 50 plaques were randomly picked up and PCR amplified each insert using T7 coat protein forward primer (5'TCTTCGCCCAGAAGCTGCAG3'SEQ ID NO: 1) and T7 coat protein reverse primer (5'CCTCCTTTCAGCAAAAAACCCC3'SEQ ID NO: 2). Filter hybridization was performed using the same Sirt2 cDNA probe as above. As shown in FIG. 2, 7 out of 50 plaques (14%) hybridized to the Sirt2 probe, a frequency similar to that observed in the plaque lifts. Plaques positively reacting with the Sirt2 probe were picked and also hybridized on Southern Blots of PCR product.

Sirt2 positive plaques (upper two rows) and Sirt2-negative plaques (lower two rows) were chosen and 1 µl (pfu indicated at left) of each amplified phage clone was spotted onto the nitrocellulose membranes which were then treated as if they were standard immunoblots using the rabbit polyclonal Sirt2 antibody (right panel) or a mouse monoclonal antibody to the T7 capsid protein (left panel). The rabbit polyclonal antibody provides a sample for testing as if it were a patient's serum using the Sirt2 protein as a model. The Sirt2 antibody in the rabbit polyclonal serum reacted specifically with the Sirt2 phage. The identity of the phage was confirmed by direct PCR sequence analysis of the cDNA inserts in two independent Sirt2 positive phage. Thus phage expressing the epitope to which the antiserum was directed were isolated and distinguished from other phage.

Microarrays were spotted using Sirt2 T7 clones and other T7 clones that do not express Sirt2. These arrays were used to analyze a mixture of Cy5-labeled (red) rabbit Sirt2-immunized serum and Cy3-labeled (green) T7 coat protein antibody (Novagen) added to the pre-immune rabbit serum. The scanned two-color image clearly shows specific detection of the Sirt2-expressing T7 clones by the anti-Sirt2 antibody. The Sirt2 expressing clones appear yellow because they bind both the red-labeled antibody to a rabbit immunoglobulin G protein and the green-labeled anti-T7 capsid 10B antibody. The non-Sirt2-expressing T7 clone are green as they only bind to the Cy3-labeled anti-T7 antibody. This development of detection of protein epitopes in bacteriophage bodes well for the applicability of phage arrays to the detection of low abundance species and weak binders. The spots in the image are approximately 100 microns in diameter.

The series of experiments provides direct evidence that biopanning a T7 coat protein fusion library can isolate epitopes for antibodies present in polyclonal sera. This also showed that the technology can be applied to direct microarray screening of large numbers of the selected phage against numerous patient and control sera. This approach provides a large number of biomarkers for early detection of ovarian cancer. The likelihood of success of this approach is increased by the fact that the mRNA for human Sirt2 is present in cells at very low abundance in human brain RNA thus indicating that clones can be isolated for rare RNA transcripts by this approach.

Figure 5:
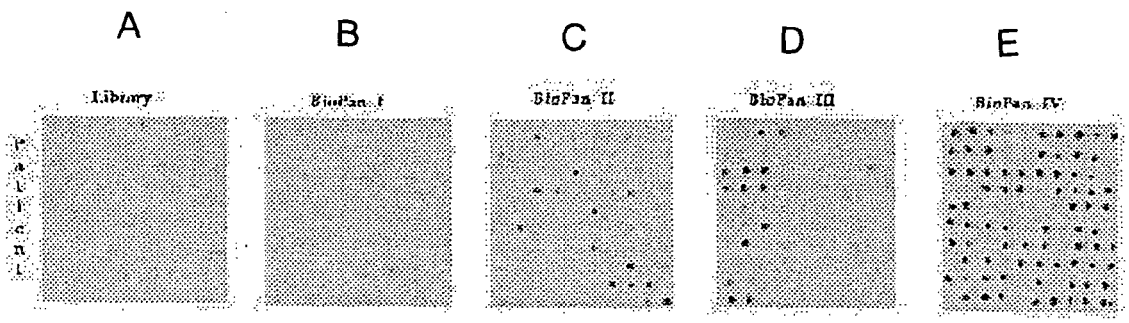
FIGS. 5A-E are photographs showing the ECL detection of phagotopes selected with a breast cancer patient's serum.
Figure 5:
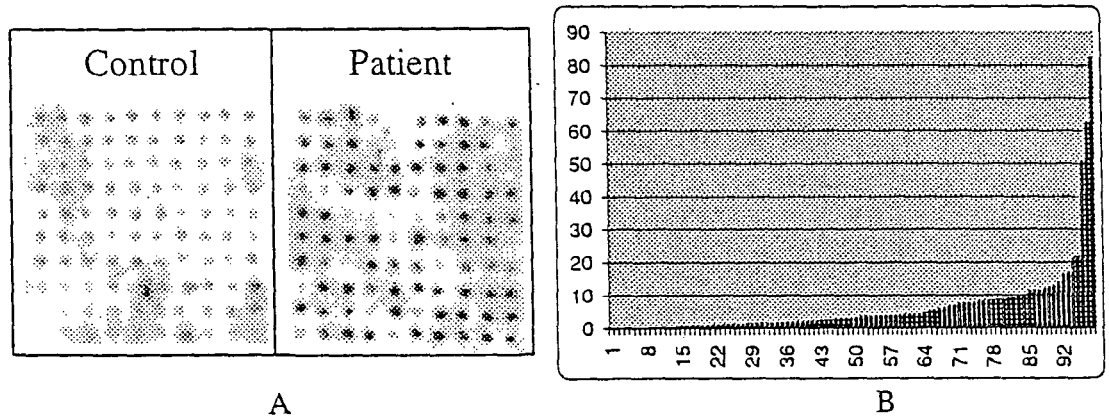
Figure 6:
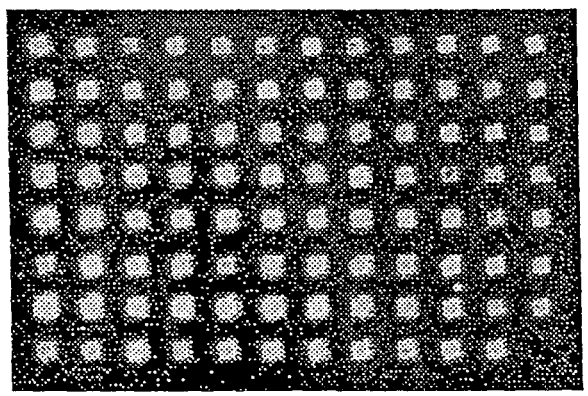
FIGS. 6A-C are as follows.

To further demonstrate the feasibility of these methods for differential detection of epitopes between test and control sera, four cycles of biopanning of a commercial Novagen breast tumor cDNA library were performed using a serum sample from a breast cancer patient and a control serum sample from a woman without cancer. 100 plaques were picked from each biopanning. Analysis of 100 plaques from the initial library and each successive biopanning were amplified in microtitre plates and the lysates cleared by centrifugation. One half microliter of each sample was spotted onto nitrocellulose filters and immunodetection performed using the breast cancer patient serum at 1:20,000 dilution (FIG. 5). Clear enrichment during biopanning is seen as was observed above with the anti-Sirt2 rabbit serum. If the biopanning had selected phage with epitopes reacting with antibodies present in the breast cancer patient serum, then there can be greater reactivity with that serum sample as compared to the reactivity using the control serum. As seen in FIG. 6 (using randomly picked plaques from BP 4) the filters contacted with the control serum on the left panels demonstrate weaker spot intensity as compared to a duplicate filter of the same clones on the right which was contacted with the patient serum. Approximately 65% of the phage selected for reactivity to the patient's serum were more than 3-fold more reactive with the patient's serum than with the control serum as determined by scanning densitometry.

FIG. 6A shows a comparison of serum reaction of control and breast cancer patient with phagotopes from BP4. FIG. 6B shows the BP4 filters which were scanned and the ratio of the pixel densities plotted in rank order.

This experiment demonstrates that one can differentially detect the epitopes for which the process is selecting, i.e. those bound to protein G-agarose beads in association with antibodies in the patient's serum and not the control serum. Someone skilled in the art can recognize that other solid supports for biopanning could replace the protein-G beads without substantively changing the biopanning process. These data also indicate that the selection is imperfect. Not all of the selected phagotopes are more reactive with the patient's serum that the control serum. Therefore, the identification of the most informative phagotopes requires analysis of the reactivity with multiple, individual patients' sera tested at various serum dilutions.

The immune reactivity to human tumors recognizes changes in the expression levels and mutation status of proteins in the tumor cells. These types of immunological reactivity are not observed in sera from control subjects. The antibody titer to tumor specific epitopes can be proportional to the tumor burden. The immune reactivity to human tumors can be used diagnostically and prognostically to predict the presence and behavior of human tumors such as tumor recurrence. Serum reactivity to single proteins tends to incompletely identify tumor bearing patients and therefore more robust methods are necessary to accurately identify tumor occurrence and recurrence. Whole genome-based proteomics such as the technology and data analysis methods embodied in the application can more comprehensively identify those proteins recognized by the host immune system.

Those of skill in the art are familiar with the construction of cDNA libraries and there are numerous published numerous papers on isolation of cDNAs from human cells in culture using this technology (Chiao, et al., 1992; shin et al., 1993; Buettner et al., 1993; Kim et al., 1996; Deyo et al., 1998; Bauer et al 1998). cDNA libraries can be prepared from ovarian cancer cell lines or from ovarian tumor tissue. Tumor tissue cDNA library can be prepared from a pool of mRNA preparations from each of the different stages of cancer to increase the diversity of clones in the library.

The following is an example of the preparation of a tumor reactive cDNA expression library: Ovarian cancer cells were grown in monolayer culture. Cells or fresh tumors from patients were lysed by the addition of 3 ml of TRIZOL reagent and the homogenized sample was incubated for five minutes at room temperature. Chloroform, 0.6 ml, was added and the mixture was shaken vigorously for 15 seconds and then incubated at room temperature for 2-3 minutes. The extract was centrifuged at 12,000×g for 30 minutes at 4° C. Following centrifugation, the mixture was separated a lower red, phenolchloroform phase, an interphase, and a colorless aqueous phase. Aqueous phase was transferred to a fresh tube and total RNA was precipitated by adding 1.5 ml of isopropanol. The mixture was incubated at room temperature for ten minutes and was centrifuged at 12,000 g for 30 minutes at 4° C. The supernatant was discarded and the RNA pellets were washed by adding 3 ml of 75% ethanol. The samples were centrifuged at 14,000×g for 15 minutes. The RNA pellet was air dried and was dissolved in RNase-free water.

mRNA was isolated from total RNA following Oligotex mRNA spin column protocol. Total RNA, 0.5 mg, was dissolved in 500 µl of RNase-free water and 500 µl of binding buffer and 30 µl of Oligotex suspension was added. The contents were mixed thoroughly, incubated for three minutes at 70° C. in a water-bath, and then at room temperature for 10 minutes. The Oligotex:mRNA complex was pelleted by centrifugation for 2 minutes at 14,000×g and the supernatant was discarded. The Oligotex:mRNA pellet was resuspended in 400 µl washing buffer by vortexing and pipetted onto a spin column placed in a 1.5 ml microcentrifuge tube. The samples were centrifuged at maximum speed for one minute and the flow-through discarded. The spin column was transferred to a new RNase-free 1.5 ml microcentrifuge tube. Elution buffer at 70° C. was then added to the column. Poly (A)$^+$ mRNA was eluted, quantitated by UV spectroscopy and the process of poly A selection repeated one more time to further reduce contamination with ribosomal RNA. Twice poly A selected mRNA was stored at −70° C. for use in library preparation.

Novagen's OrientExpress cDNA Synthesis and Cloning systems were used for the construction of ovarian cancer cDNA T7 phage libraries. For first-strand cDNA synthesis, OrientExpress Random Primer System was used to ensure representation of both N-terminal and C-terminal amino acid sequences.

Ten ml of LB/carbenicilln medium were inoculated with a single colony of BLT5615 from a freshly streaked plate. The mixture was shaken at 37° C. overnight. Ten ml of the overnight culture was added to 90 ml of LB/carbenicillin medium and was allowed to grow until $OD_{600}$ reaches 0.4-0.5. IPTG (1 mM), M9 salts (1×) and glucose (0.4%) can be added and the cells were allowed to grow for 20 minutes. An appropriate volume of culture was infected with phage library at MOI of 0.001-0.01 (100-1000 cells for each pfu). The infected bacteria were incubated with shaking at 37° C. for one to two hours until lysis is observed. Glycerol (0.02%), PMSF (0.02M) was added to the cell lysate to block proteolysis of the capsid fusion proteins. The phage were centrifuged at 8000×g for 10 minutes. The supernatant was collected and was stored at 4° C. The lysate was titered by plaque assay under standard conditions. The libraries are stored after purification by polyethylene-glycol precipitation and ultracentrifugation through a stepwise CsCl gradient.

Using this approach applicants have constructed the first library. Using twice poly A selected mRNA from SKOV3 cells a T7 select cDNA library was prepared containing 1.8× $10^7$ initial plaques after packaging. This representation is comparable to the clonal representation of the commercial libraries purchased. This library has been amplified and stored in aliquots in two −70° C. freezers.

Patients' sera were obtained from multiple institutions for this project. Three outside institutions have agreed to provide ovarian cancer patient sera and the associated medical record information in anonymized form. Dr. Steven Witkin from the Weill Medical College of Cornell University provided 46 patient serum samples and 27 controls. Dr. Karen Lu from the M.D. Anderson Cancer Center can provide 60 serum samples. Dr. David Fishman from the Northwestern University Comprehensive Cancer Center provided 35 serum samples of patients who have been followed from time of diagnosis.

The ideal sera for the clone biopanning studies come from women just before or after surgery and prior to chemotherapy. Follow up sera were obtained after chemotherapy and are important to determine whether the penultimate protein array technology can detect tumor recurrence.

In addition, a supply of tumor tissue was required for the preparation of mRNA for cDNA library production and gene expression studies using samples from DMC patients. This tissue was harvested within 20 minutes of surgical excision from the patients. This requires the coordinated effort of the gynecologic surgeons and pathologists. Patients at the time of their original surgery or prior to chemotherapy were accrued for serum collection. If tumor tissue is available in excess of that needed for routine pathologic evaluation, that tissue was used for RNA preparation for mRNA expression studies associated with this study. Sections from tissue blocks were also acquired for the purpose of expression studies of proteins in the patients' tumors. Patients at follow up visits to the OB/GYN clinics were also subjects for serum acquisition. These latter patients can be at a time of recurrence or not. This allows the observation of the reappearance of serum markers in the event of tumor recurrence. Serum was obtained from eligible patient-subjects during scheduled clinic visits. The initial serum acquisition occurs prior to surgery, if possible, or if post surgery, prior to chemotherapy. A single red top 7 cc vial of blood was obtained during normal phlebotomy and the serum isolated after clotting. Serum continues to be collected from these patients during follow up visits for up to five years or until ovarian cancer recurrence. Tumor tissue in excess of that required for pathological analyses were acquired at the time of surgery for the preparation of tumor RNA needed for antibody screening. Unaffected volunteers (controls) were be recruited through community outreach activities.

For the purpose of comparison to the ovarian cancer patients, one can also analyze serum markers in women in good health who do not have ovarian or any other type of cancer. These control subjects should not have a family history of ovarian cancer or breast cancer. Because some serum markers such as CA125 levels are increased in endometriosis, uterine leiomyoma, pelvic inflammatory disease, early pregnancy, and benign cysts, control subjects should be free of these conditions as well.

The purpose of this study is to clone epitopes that are recognized by sera from women with ovarian cancer but not recognized by normal sera from unaffected women. As these epitopes are cloned, protein array assays are developed capable of detecting ovarian cancer at an early stage by analyzing antigens recognized in the sera of at risk women. Toward this end, individual sera were screened using these protein biochips to determine the antibody reactivity to each protein epitope. Antibody reactivity is detected that does not appear in control sera. The patients and control sera obtained for this study were used to calibrate the protein biochips and identify the most informative epitope-clones. The women were monitored for the appearance or reappearance of antibody reactivity and its correlation with tumor burden. By following the serum reactivity to tumor reactive new epitopes on the arrays of the phage display cDNA clones, the analysis of sera from women after their initial diagnosis and semiannually thereafter allows us to determine the utility of these markers in predicting tumor recurrence.

If some of the markers prove to be predictive of recurrence, then it can be important to determine if there is any correlation with some specific ovarian tumor types (using the World Health Organization Histological Classification of Ovarian Tumors), also the tumor grade (where appropriate, since not all tumors all graded), and the surgical stage. This can done by review of the pathological material (glass slides, patient records, and surgical pathology reports). Certain currently accepted biomarkers of research interest such as Her-2 neu and other can also be included in the new protein biochips in order to compare the sensitivity and specificity of the new and existing immunohistochemical technologies. Testing for Her-2 neu and other biological markers is done by the immunoperoxidase method using formalin fixed, paraffin embedded tumor tissues.

Steps in the Biopanning Process: Affinity selection with sera from normal individuals: Twenty-five µl of Protein G Plus-agarose beads were taken in 0.6 µl eppendorf tube and were washed two times with 1×PBS. Washed beads were blocked with 1% BSA at 4° C. for one hour. The beads were then incubated at 4° C. for one hour with 250 µl of pooled sera at a dilution 1:20 from 20 control women. After three hours of incubation, beads were washed three times with 1× PBS and then incubated with phage library (~$10^{10}$ phage particles). After incubation, the mixture was centrifuged at 3000 rpm for two minutes to remove phage nonspecifically bound to the beads and the supernatant (phage library) was collected for immunoscreening.

Fresh protein G Plus agarose beads were placed into a 0.6 ml eppendorf tube and were washed two times with 1× PBS. Washed beads were blocked with 1% BSA at 4° C. for one hour. The beads were then incubated at 4° C. for three hours with 250 µl of sera at a dilution 1:20 from patients with ovarian cancer. After this incubation, the beads were washed three times with 1× PBS and were incubated with phage library supernatant from above (termed as Biopanning 1 (BP1)) collected for immunoscreening at 4° C. for overnight (shorter times of incubation have not proven successful using model antibody systems). After incubation, the mixture was centrifuged at 3000 rpm for two minutes and supernatant can be discarded. Beads were washed three times with 1×PBS. To elute the bound phage 1% SDS was added to the washed beads and the mixture was incubated at room temperature for ten minutes. The bound phage were removed from the beads by centrifugation at 8000 rpm for seven minutes. Eluted phage were transferred to liquid culture for amplification (100 µl elution to 20 ml culture). Four rounds of affinity selection and immunoscreening was carried out with amplified phage obtained after each biopanning. The number of biopanning cycles generally determines the extent of the enrichment for phage that binds to the sera of patient with ovarian cancer. This process allows for one cycle of biopanning to be performed in a single day.

In the past serum markers have been identified using SEREX technology that detected only a few gene products at a time. The biopanning approach developed can isolate large numbers of target epitopes. These epitopes are displayed on the surface of bacteriophage as in-frame fusion proteins with the T7 phage capsid protein and can be analyzed in large numbers by arraying the selected phage on filter paper or glass slides (protein microarrays). The method isolates large numbers of phage that react with antibodies from pooled patient sera but not with normal sera.

The titer of the T7 phage library obtained after amplification of each Biopanning (BP1-4) eluate was determined by plaque assay. E. Coli BLT 5616 were infected with the primary unamplified phage from biopanning (BP3-4) and plaqued to limiting dilution onto LB/carbenicillin plates (150 mm×15 mm petri dish) so that sufficient numbers of single plaques can be isolated to obtain 12×96 well plates for arraying. The plates were incubated at 37° C. for 3-4 hours until the plaques are visible and then picked for amplification in the 12×96 well plates. After two hours, lysis of the host bacteria occurs in the wells of the 96-well plates. One well of each plate was uninfected as a control. Five 96 well plates of 200 µl phage lysates are clarified by centrifugation of the phage. The phage were cleared by whole plate centrifugation before robotic spotting in triplicate onto filters or glass slides. Excess reactivity in the surface area of the slide not spotted with phage is blocked using BSA, 1% solution in PBS for 60 minutes, followed by washing in water three times. After blocking the arrays on glass slides or filters were blocked with 1% BSA in PBS and incubated with a various dilutions of each of the individual controls and patient's sera spotted in triplicate or more for each dilution of serum. Serum antibodies binding to recombinant proteins expressed in the surface of the T7 bacteriophage were detected by incubation a Cy5-labeled anti-human IgG goat antiserum and visualized and quantified using GenePix and ImaGene software in a 4000B array scanner (AXON Instrument). As positive control for each spot a Cy3-labeled antibody for the T7 capsid protein was used. The ratio of the fluorescence intensity for the human antibodies were normalized to the T7 capsid antibody reactivity. Initial testing of phage solutions were performed on a spotting robot.

The optimal number of subtractive biopannings for each serum sample is determined by picking individual phage clones, and then testing the antibody reactivity for the serum used in the biopanning against those clones, (referred to as its self reaction). Plates of 96 clones were picked for each patient's biopanning at cycles 3, 4, and 5 which were then tested for the binding of the phage clones to antibodies in that serum, in a "self-reaction". Antibody binding is detected by spotting the filters with a 96 pin head on a Biomek robot or detected on glass slides of microarrays of phagotopes. The filters are then treated like a western blot by blocking with 1% dry milk powder in PBS and adding diluted serum. After rocking for 2 hours the filter is washed and reacted with an anti-human IgG antibody link to horseradish peroxidase (HRP) and detected by ECL. From the clones isolated from one patient, (designated patient #1) a total of 480 plaques were picked from that serum at biopanning 4. Biopanning four was chosen because about 35% of the clones bound antibodies from that patient's serum. Serum reactivity of the phagotopes with the patient's serum was detected at a 1:10,000 dilution indicating a very high titer of the IgG molecules that react with the epitopes (self reaction with 480 clones). Reactivity to these clones is detected at similar dilutions using the clones arrayed on glass slides as an alternative solid support.

When the serum reactivity with other patients (non-self reactions) was analyzed using replicates of the robotically spotted filters, reactivity was found in some patients again at a dilution of 1:10,000 (FIG. 1b). Other patients required a 1:3000 dilution of the serum for detection of the reactive clones Table 1). Patients #23 reacted quite strongly while patient #16 reacted more weakly (FIG. 1b and Table 1). Positivity was scored only when 3 out of 3 of the triplicates have similar intensity. In the subtractive biopanning scheme plaques binding to normal serum proteins nonspecifically were removed by loading protein-G beads with a pool of control sera. One can detect positive reaction on filters spotted with phage epitope clones on filter 13 of 21 other patients using 153 reactive clones of the original 480 clones. Filters were tested with control sera not used in the initial subtractive step, and 5 of the 8 controls showed no reaction to the 480 phage on the filter arrays while a non-specific and even pattern of reactivity to all clones (without the typical triplicate pattern) was observed using 3 of the 8 different control sera (Table 1).

| Patient's sera | # of phage Patient #1 BP4 clones reacted with each patient's sera at indicated dilution | |
|---|---|---|
| | 1:10000 | 1:3000 |
| PATIENT 1 | 153 (self reaction) | |
| PATIENT 2 | None | 142 |
| PATIENT 16 | NS | |
| PATIENT 20 | 70 | |
| PATIENT 23 | 137 | |
| PATIENT 29 | NS | |
| PATIENT 30 | NS | |
| PATIENT 33 | NS | |
| PATIENT 35 | NS | 72 |
| PATIENT 37 | None | 120 |
| PATIENT 01-056 | NS | |
| PATIENT 01-060 | None | 61 |
| PATIENT 00-007 | NS | |
| PATIENT 01-108 | NS | |
| PATIENT 01-045 | NS | |
| PATIENT 42501 | 40 | |
| PATIENT 400162 | 120 | |
| PATIENT 40036 | Mostly NS | |
| PATIENT 42780 | 85 | |
| PATIENT B755 | NS | |
| PATIENT 40015 | NS | |
| PATIENT 075 | 119 | |
| PATIENT 015 | 155 | |
| PATIENT 035 | NS | |
| PATIENT 007 | 114 | |
| PATIENT 005 | 133 | |
| PATIENT 083 | 150 | |
| PATIENT 054 | 92 | |
| PATIENT 064 | NS | |
| PATIENT 065 | NS | |

NS indicates Non-Specific reaction only; None indicates No reaction detected.

The filter arrays are incubated with a patient's serum (pre-treated with 150 µg of bacterial extract to block nonspecific reactions with E. coli proteins for 2 hours at 4° C.) at various dilutions for 1 hour at room temperature. Bacterial extracts are used because some patients have antibodies to bacterial protein, and therefore pre-treatment with extracts of E. coli proteins blocks the nonspecific antibodies to bacterial protein present in the patient's serum. The membranes are then washed three times with TBST (0.24% Tris, 0.8% NaCl, and 1% Tween-20) for 15 minutes each. After washing is completed, the membranes are incubated with secondary antibody, goat-anti human IgG-HRP conjugated (Pierce) at 1:5000 dilution for 1 hour at room temperature. The membranes are again washed three times with TBST 15 minutes each. Finally, membranes are developed with Supersignal West Pico chemiluminescent substrate (Pierce) and the images were captured on a Kodak film.

Phagotope Microarrays on Glass Biochips Preparation of Arrays Phage lysates are prepared as above. Phage lysates (usually five 96 well plates) from BP4 are transferred to 384-well plates, each lysate spotted in quadruplicate, using 10 µl per well. A robotic microarrayer is used to spot the phage in an ordered array onto FAST™ slides (Schleicher & Schuell) at a 350 µm spacing using 4 steel Micro-Spotting Pins. The arrays are dried overnight at room temperature.

Preparation of Fluorescent Antibody Probes T7 monoclonal antibody and goat anti-human IgG are purchased from Novagen and Pierce respectively. Monofunctional NHS-ester activated Cy3 and Cy5 dyes are purchased from Amersham (PA33001 and PA35001). The antibodies are labeled in pH 8.0 sodium carbonate buffer as per the instructions from the manufacturer. Briefly, 100 µl of the protein solution with 5 µl of coupling buffer is transferred to the vial of reactive dye and mixed thoroughly. The reaction is incubated in the dark at room temperature for 30 minutes with additional mixing approximately every 10 minutes. The reaction solutions are then loaded into the gel filtration columns to separate the labeled protein from non-conjugated dye. T7 antibody is labeled by Cy3 and anti-human IgG is labeled by Cy5, respectively. The labeled protein is eluted and stored at 4° C. for future use. Reversing the dye labeling scheme of the antibodies does not affect the results. The advantage of this strategy is that the same reagents were used on every phagotope array and the only variable is the patient's serum and therefore variations in labeling efficiency are not a factor.

Detection of Fluorescent Antibody Probes The arrays are rinsed briefly in a 1% BSA/PBS to remove unbound phage, transferred immediately to 1% BSA/PBS as a blocking solution, and then incubated in this blocking solution for 1 hour at room temperature. The excess BSA is rinsed off from the slides using PBS. Without allowing the array to dry, 2 ml of PBS containing human serum at a dilution of 1:10,000 is applied to the surface in a screw-top slide hybridization tube. Multiple dilutions are tested per patient to otain optimal detection. The arrays are incubated at room temperature for 1 hour with mixing. The arrays are rinsed in PBS to remove the serum, and then washed gently three times in PBS/0.1% Tween-20 solution 10 minutes each. All washes are performed at room temperature. After removing Tween-20 using PBS, the arrays are incubated with 2 ml of PBS containing Cy3-labeled-T7 anti-capsid antibody at a dilution of 1:50,000 and anti-human IgG labeled with Cy5 at a dilution of 1:10,000 as probes for 1 hour in the dark. The incubation solution is mixed every 20 minutes. Three washes are performed using PBS/0.1% Tween-20 solution with 10 minutes each. The array is then rinsed with filtered ddH$_2$O twice and dried using a stream of compressed air.

Analysis Phagotope Microarrays The arrays are scanned in an Axon Laboratories scanner (Axon Laboratories, Palo Alto, Calif.) using 532 nm and 635 nm lasers. The ratio of anti-T7 capsid and anti-human IgG is determined by comparing the fluorescence intensities in the Cy3- and Cy5-specific channels at each spot. The location of each spot on the array is outlined using the image processing software. The background, calculated as the median of pixel intensities from the local area around each spot, is subtracted from the average pixel intensity within each spot. This normalized reactivity is entered into a database for analysis.

The information in this database can be analyzed in order to: i) select the most informative epitopes and ii) develop into a diagnostic test for tumor occurrence in high risk women or tumor recurrence in women previously treated for ovarian cancer. The gene products thusly identified can provide insight into molecular changes recognized by the host immune system.

The human antibodies reacting at each spot are detected with Cy5-labeled human serum antibodies. The normalization of the fluorescence at each spot is compared to a reaction with a Cy3-labeled antibody to the T7 phage capsid protein. Only a small fraction of the phage capsid protein is substituted with the in-frame fusion of the human cDNAs of the library. The majority of the capsid protein is produced by the host bacterium from an episomal T7-capsid gene. Therefore the majority of the each capsid protein is wild-type and can react with the anti-capsid antibody. An example of a Cy5 labeled anti-human IgG reacting with IgG in patients #1 serum bound to clones biopanned using patient #1 serum is shown in FIG. 6*c*.

The data analysis proceeds according to the following steps:
4. Pre-processing and normalization.
5. Identifying the most informative markers
6. Building a predictor for molecular diagnosis of ovarian cancer and validating the results.

The pre-processing and normalization step is used for arrays using two channels such as Cy5 for the human IgG and Cy3 for the T7 control. The spots are segmented and the mean intensity is calculated for each spot. A mean intensity value is calculated for the background, as well. A background corrected value is calculated by subtracting the background from the signal. If necessary, non-linear dye effects can be eliminated by performing an exponential normalization (Houts, 2000) and/or a piece-wise linear normalization of the data obtained in the first round. The exponential normalization can be done by calculating the log ratio of all spots (excluding control spots or spots flagged for bad quality) and fitting an exponential decay to the log (Cy3/Cy5) vs. log (Cy5) curve. The curve fitted is of the form:

$$y=a+b*\exp(-cx)$$

where a, b and c are the parameters to be calculated during curve fitting. Once the curve is fitted, the values are normalized by subtracting the fitted log ratio from the observed log ratio.

This normalization has been shown to obtain good results for cDNA microarrays but it relies on the hypothesis that the dye effect can be described by an exponential curve. The piece-wise linear normalization can be done by dividing the range of measured expression values into small intervals, calculating a curve of average expression values for each such interval and correcting that curve using piece-wise linear functions.

The values coming from each channel are subsequently divided by the mean of the intensities over the whole array. Subsequently, the ratio between the IgG and the T7 channels was calculated. The values coming from replicate spots (spots printed in quadruplicates) are combined by calculating mean and standard deviation. Outliers (outside+/−two standard deviations) are flagged for manual inspection). Single channel arrays are pre-processed in a similar way but without taking the ratios. This preprocessing sequence was shown to provide good results for all preliminary data analyzed.

The step of selecting the most informative markers is used to identify the most informative phages out of the large set of phages started with. The better the selection, the better is the expected accuracy of the diagnosis tool. A first test is necessary to determine whether a specific epitope is suitable for inclusion in the final set to be spotted.

Procedure 1

This is started by defining the template for the cancer case shown in FIG. 8. Each epitope can have a profile across the given set of patients (FIGS. 9A and B). The profile of each epitope is compared with the templates using a correlation-based distance.

The epitopes are then ordered based on the similarity between the reference profile (FIG. 8A) and their actual profile. FIG. 12 shows 46 epitopes found informative for a correlation threshold of 0.8. The final cutoff threshold is calculated by doing 1000 random permutations once the whole data set become available. Each such permutation moves randomly the subjects between the 'patient' and 'control' categories. Calculating the score of each epitope profile for such permutations allows us to establish a suitable threshold for the similarity.

In order to reduce the effect of controls with a non-specific response, all such subjects (i.e a unimodal distribution such as in the left panel of FIG. 13) were eliminated from the analysis leading to the epitope selection.

Procedure 2 is used to maximize the information content of the set of epitopes while trying to minimize the number of epitopes used using the following procedure.

Procedure 2

Assume there are m patients and k controls. Select n random patients from the m available. For each of the n patients used for epitope selection, amplify (n×4 biopannings) and do self reactions. Eliminate those patients/epitopes that do not react to self.

Make a chip with all available, self-reacting epitopes printed in quadruplicates. React this chip with all patients and controls (n+k antibody reactions). Eliminate controls with a non-specific reactivity. For the set of epitopes coming from a single patient, apply Procedure 1 to order the epitopes in the order of their informational content and select the ones that can be used to differentiate patients from controls.

Order the epitopes by their reactivity in decreasing order of the number of patients they react to. Scan this list from the top down, moving epitopes from this list to the final set. Every time a set of epitopes coming from a patient x is added to the final set, the patient x and all other patients that these epitopes react to are represented in the current set of epitopes. Repeat until all patients are represented in the current set of epitopes.

The arrays used in this example, (using two channels such as Cy5 for the human IgG and Cy3 for the T7 control) are processed as follows. The spots are segmented and the mean intensity is calculated for each spot. A mean intensity value is calculated for the background, as well. A background corrected value is calculated by subtracting the background from the signal. The values coming from each channel are normalized by dividing by their mean. Subsequently, the ratio between the IgG and the T7 channels are calculated and a logarithmic function is applied. The values coming from replicate spots (spots printed in quadruplicates) are combined by calculating mean and standard deviation. Outliers (outside+/−two standard deviations) are flagged for manual inspection.

The histogram of the average log ratio is calculated. If the histogram is unimodal (e.g subject 19218 in FIG. 13), there is no specific response. If the histogram is clearly bimodal (e.g. subject 19223 in FIG. 13), there is a specific response. All 25 subjects analyzed so far fell in one of these two categories or had no response at all. The preliminary data analyzed so far showed a very good separation of the distributions for the patients.

Once the chosen clones are spotted on the final version of the array, a number of sera coming from both patients and controls can be tested. These sera come from subjects not used in any of the phases that lead to the fabrication of the array (i.e. not involved in clone selection, not used as controls, etc.). Each test was evaluated using Procedure 3 above.

Building the Predictor

A number of machine learning and statistical techniques have been considered for this task. The following algorithms were tested: CN2 (Clark, 1989), C4.5 (Quinlan, 1993; Breiman et al., 1984), CLEF 1998), 4.5 using classification rules (Quinlan, 1993), incremental decision tree induction (ITI) (Utgoff, 1989; quantization (LVQ) (Kohonen, 1988; Kohonen, 1995), induction of oblique trees (OC1) (Health and Salzberg, 1993; Murthy, 1993), Nevada backpropagation (NEVP); Rumelhart et al., 1987), Constraint Based Decomposition (Draghici, 2001), k-nearest neighbors with k=5 (K5), Q* and RBF's (Musavi et al., 1992; Poggio and Girosi, 1990).

The generalization abilities and the reliability of these techniques have been tested extensively on various problems and data sets from the UCI machine learning repository (Blake et al., 1998). This repository contains a large collection of mostly real world data from a large variety of domains (including biological and medical), and constitutes a benchmark on which various algorithms and techniques can be tested.

Table 2 presents the accuracies obtained by these techniques on the selected problems. Table 3 presents the standard deviation of each such algorithm on the same problems. Based on these tests applicant decided to start the tests by using constraint based decomposition (CBD), radial basis functions (RBFs) and decision trees (C4.5) as the three main candidates. The CBD was selected because it offers a high reliability across multiple trials (lowest standard deviation) and a good accuracy (second best). Furthermore, the CBD algorithm can also produce a logical expression describing the classifier produced. Such expressions allow one to understand the relative importance of various epitopes. The decision trees have been selected mainly because they can be mapped into logical expressions that can be compared to the one produced by the CBD. RBFs construct clusters by placing high dimensionality Gaussian functions on groups of given data points (one data point can be a set of expression values corresponding to a protein chip). This technique calculates automatically the number of clusters, their orientation (the eigenvectors of the correlation matrix of the expression vectors) and their widths. RBFs were expected to perform much better than k-means clustering and the other techniques already used in this context because RBFs avoid guessing (e.g. k in k-means clustering). Furthermore, extracting a model from the trained RBF architecture is straightforward. Again, this model can be compared with the models provided by the CBD and C4.5

| DATASET | C4.5 | C4.5r | ITI | LMDT | CN2 | LVQ | OC1 | NEVP | K5 | Q* | RBF | CBD |
|---|---|---|---|---|---|---|---|---|---|---|---|---|
| GLASS | 70.23 | 67.96 | 67.49 | 60.59 | 70.23 | 60.69 | 57.72 | 44.08 | 69.09 | 74.78 | 69.54 | 68.37 |
| IONO-SPHERE | 91.56 | 91.82 | 93.65 | 86.89 | 90.98 | 88.58 | 88.29 | 83.8 | 85.91 | 89.7 | 87.6 | 88.17 |
| LUNG CANCER | 40.17 | 39.84 | 38.47 | 55.49 | 37.17 | 55.71 | 54.28 | 33.12 | 68.54 | 60 | 65.7 | 60 |
| WINE | 91.09 | 91.9 | 91.09 | 95.4 | 91.09 | 68.9 | 87.31 | 95.41 | 69.49 | 74.35 | 67.87 | 94.44 |
| PIMA INDIANS | 71.02 | 71.55 | 73.16 | 73.51 | 72.19 | 71.28 | 50 | 68.52 | 71.37 | 68.5 | 70.57 | 68.72 |

-continued

| DATASET | C4.5 | C4.5r | ITI | LMDT | CN2 | LVQ | OC1 | NEVP | K5 | Q* | RBF | CBD |
|---|---|---|---|---|---|---|---|---|---|---|---|---|
| BUPA | 65.14 | 65.39 | 63 | 71.54 | 64.31 | 64.13 | 65.57 | 77.72 | 66.43 | 61.43 | 59.85 | 62.32 |
| TICTAC-TOE | 83.52 | 99.17 | 92.89 | 89.61 | 98.18 | 65.61 | 78.56 | 96.91 | 84.32 | 65.7 | 72.19 | 75.1 |
| BALANCE | 64.61 | 75.01 | 76.76 | 93.27 | 80.89 | 89.54 | 92.5 | 91.04 | 83.96 | 69.21 | 89.06 | 90.08 |
| IRIS | 91.6 | 91.58 | 91.25 | 95.45 | 91.92 | 92.55 | 93.89 | 90.34 | 91.94 | 92.1 | 85.64 | 96 |
| ZOO | 90.27 | 90 | 90.93 | 96.61 | 91.91 | 91.42 | 66.68 | 92.86 | 67.64 | 74.94 | X | 94.29 |
| AVG | 75.92 | 78.42 | 77.87 | 81.84 | 78.89 | 74.84 | 73.48 | 77.38 | 75.87 | 73.07 | 74.22 | 79.75 |

Table 2 shows a comparison of several classification techniques. The table presents the accuracies obtained in various problems from the UCI machine learning respiratory. Each accuracy is the average of 10 trials.

| DATASET | C4.5 | C4.5r | ITI | LMDT | CN2 | LVQ | OC1 | NEVP | K5 | Q* | RBF | CBD |
|---|---|---|---|---|---|---|---|---|---|---|---|---|
| GLASS | 7.23 | 6.28 | 7.96 | 11.25 | 8.34 | 10.24 | 9.1 | 6.29 | 7.81 | 6.98 | 7.35 | 2.08 |
| IONOSPHERE | 2.82 | 2.58 | 2.71 | 3.51 | 3.29 | 3.36 | 2.21 | 3.81 | 4.14 | 4.7 | 6.45 | 2.56 |
| LUNG CANCER | 14.2 | 18.92 | 13.52 | 32.2 | 13.79 | 12.48 | 17.53 | 14.83 | 11.96 | 18.6 | 16.27 | 12.6 |
| WINE | 5.84 | 5.09 | 6.24 | 5.22 | 6.11 | 4.84 | 8.45 | 2.22 | 6.86 | 6.64 | 5.16 | 1.96 |
| PIMA INDIANS | 2.1 | 3.92 | 2.16 | 4.3 | 2.36 | 4.46 | 22.4 | 3.19 | 3.67 | 8.19 | 2.39 | 3.02 |
| BUPA | 5.74 | 6.05 | 4.23 | 6.63 | 7.99 | 7.14 | 8.45 | 11.97 | 7.22 | 4.25 | 7.92 | 2.05 |
| TICTAC-TOE | 2.44 | 1.05 | 2.38 | 8.79 | 0.95 | 2.99 | 5.88 | 1.32 | 2.7 | 3.16 | 3.35 | 9.43 |
| BALANCE | 3.35 | 3.98 | 3 | 2.95 | 3.38 | 4.39 | 2.07 | 7.12 | 7.53 | 19.09 | 2.38 | 3.03 |
| IRIS | 5.09 | 5.09 | 4.81 | 4.71 | 5.95 | 3.73 | 4.68 | 7.45 | 4.1 | 5.28 | 27.37 | 4.35 |
| ZOO | 7.59 | 7.24 | 6.11 | 1.56 | 5.95 | 6.26 | 30.36 | 4.62 | 20.03 | 23.8 | X | 2.13 |
| AVG | 5.64 | 6.02 | 5.312 | 8.112 | 5.811 | 5.989 | 11.11 | 6.282 | 7.602 | 10.07 | 8.738 | 4.321 |

Table 3 shows a comparison of several classification techniques. The table presents the standard deviations obtained in a set of 10 trials on various problems from the UCI machine learning repository.

Furthermore, one can also implement and try the predictors used in (Golub et al., 1999) and (Alizadeh et al., 2000) which were shown to work well in cancer diagnosis problems similar to applicant's. The selection of the final predictor was based on the validation results obtained in the last step of the data analysis.

Validating the Predictor

In order to validate the predictors, the classical method of cross-validation was used (Breiman et al., 1984). The idea behind cross-validation is that the predictor is tested, not based on its abilities to simply memorize the data presented during the training, but based on its abilities to generalize the knowledge acquired during the training to previously unseen cases. For this reason, the predictor must be checked on data that belongs to the same distribution but was not used during the training. This can be implemented in several ways depending on the number of examples available. If only few examples (such as stage I patients, ~40 total) are available, reducing the size of the training set even further by setting patterns aside for generalization testing could jeopardize the training. In such cases, the algorithm is used with only n−1 of the n available patterns and tested on the remaining one. This is done n times, each time leaving out a different pattern. An average is calculated over the n experiments. This is known as the leave-one-out method. If more patterns are available, the pattern set can be divided into n different subsets of patterns. Then one subset can be left out of the training and used to test the generalization. Again, the value reported is an average of the n trials performed leaving out each of the n subsets. This method is known as n-fold cross validation. Finally, if the pattern set is very large (patients with stage III or IV cancer), it can simply be divided into a training set and a validation set. In this case, the generalization abilities of the technique can be characterized by its performance on the validation set.

For each predictor the specificity, sensitivity, positive predictive value and negative predicted value can be calculated using cross-validation data (i.e. values that have not been used in constructing the predictor itself). This ensures that the quality measures obtained in this study reflects the real world performance to be expected in the field.

Once informative phagotopes are found the gene encoding the phagotope was identified.

1. Identification genes encoding the phagotopes. Phage clones specifically reacting with patient sera, as determined by microarray immunoscreening, can be amplified by PCR using T7 capsid forward and reverse primers. PCR fragments were purified and 100 ng of fragment was analyzed to determine the nucleotide sequence of the cDNA insets. Sequence alignments are performed using BLAST™ software (Basic Local Alignment Search Tool (BLAST) finds regions of local similarity between sequences, the program compares nucleotide or protein sequences to sequence databases and calculates the statistical significance of matches.) and GenBank™ data bases (GenBank is the NIH genetic sequence database). The sequence information can be used in several ways. Initially, the DNA sequence information provides a database of the frequency of reactivity to a particular epitope.

Diagnostic Markers Derived from the Combined Processes Including Biopanning, Assay of Patients' Sera with Epitopes on Filters and Biochips, and Identifying the Best Predictor of Disease DNA Sequence Analysis of Phagotope Clones PCR amplified DNA sequences from 96 phagotopes that reacted with patient #1 and at least one other OVCA serum are shown in the table below. Some clones were isolated multiple times and one clone was represented 23 times out of the 96 clones analyzed. This was the human homologue of the oncogenic gene Bmi-1, (GenBank NM005180.1) that inhibits the expression of p14ARF and cooperates with c-myc (Lindstrom et al., 2001. The insert sizes for the Bmi-1 phage clones varied in coding capacity depending on the isolate between 67-94 amino acids in length. Eight other clones were represented twice and one was isolated three times. One of these genes isolated twice was the heat shock protein 70, which has been shown to be overexpressed and antigenic in ovarian cancer tumors and was found to have been identified in the SEREX database 5 times. The size of the open reading frame in the HSP70 clone is 109 amino acids in length. Another clone isolated two times of the 96 sequenced is a known cancer antigen called RCAS1 which is overexpressed in 58% of ovarian cancer and many others as well (Sonoda et al., 1996) RCAS1 is an estrogen regulated gene which can inhibit the immune system from killing a tumor (Nakashima et al., 1999). This information clearly indicates that this technology is capable of detecting cancer antigens which can be used for diagnostic and immunotherapy purposes. If overbiopanning occurred, only a few different clones would be found. However, as the remaining clones were isolated once each, it is therefore convincing that 4-5 biopannings is appropriate. In this first group of 480 clones there were isolated clones that reacted with approximately 60% of the OVCA patients using the macroarray filters and more efficiently using the microarray technology. Additional epitope clones provide additional sensitivity for this assay.

| Clone Name | GenBank ID |
|---|---|
| Clone found 23 times Bmi-1 (oncogene) | NM_005180.1 |
| Clones found 2-3 times | |
| HSP-70 | XM_050984.1 |
| RCAS1 (EBAG9) | BC005249.1 |
| A-kinase anchoring protein 220 | XM_038666.1 |
| G-protein gamma-12 subunit | NM_018841.1 |
| Neuronal apoptosis inhibitory protein 6 | AF242431.1 |
| hypothetical protein DC42 | XM_028240.1 |
| WD repeat domain 1 (WDR1) | XM_034454.1 |
| zinc finger protein 313 | XM_009507.1 |
| 54 other clones isolated once each | |

Summary

Serum reactivity toward a cellular protein can occur for two possible reasons: 1) expression of a mutated form of the protein by the tumor cells and 2) overexpression of the protein in the tumor cells. Identification of proteins detected by the host immune system in this fashion therefore provides patienthanistic information about protein(s) that can be mutated or overexpressed in ovarian cancer. Such information provides insight into the molecular targets and mechanisms giving rise to ovarian cancer. Lastly, the sequences identified using the epitope-biopanning/phage microarray approach can be useful for early detection of cancer occurrence and recurrence by screening patients' sera and peritoneal fluids and providing immunogens for immunotherapy vaccines.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. Alizadeh A A, et al. Distinct types of diffuse large B-cell lymphoma identified by gene expression profiling. Nature 403:503-511, (2000).

2. An, A, et al. A learning system for more accurate classifications. Lecture Notes in Artificial Intelligence, Vancouver. 1418:426-441, (1998).

3. Aunoble B, et al. Major oncogenes and tumor suppressor genes involved in epithelial ovarian cancer. Int J Oncol 16:567-76, (2000).

4. Baron A T, et al. Serum sErbB1 and Epidermal Growth Factor Levels As Tumor Biomarkers in Women with Stage III or IV Epithelial Ovarian Cancer Epidemiology. Biomarkers & Prevention 8:129-137, 1999.

5. Bauer R, et al. Cloning and characterization of the Drosophila homologue of the AP-2 transcription factor. Oncogene 17:1911-1922 (1998).

6. Bast R C, et al. Reactivity of a monoclonal antibody with human ovarian carcinoma. J. Clin Invest 68:1331-1337 (1981).

7. Bast R C et al. A radioimmunoassay using a monoclonal antibody to monitor the course of epithelial ovarian cancer. N Engl J Med 309: 883-887 (1983).

8. Berek, J S et al. Serum interleukins-6 levels correlate with disease status in patients with epithelial ovarian cancer. Am J Obstet Gynecol 164: 1038-1043 (1991).

9. Bittner, M et al. Molecular Classification of Cutaneous Malignant Melanoma by Gene Expression Profiling. Nature 406:536-540 (2000).

10. Blake C, et al. UCI respitory of machine learning databases (1998).

11. Boyd J, et al. Molecular genetic and clinical implications [Review]. Gynecol Oncol 64:196-206 (1997).

12. Breiman L, et al. Classification and regression trees, Wadsworth and Brooks (1984).

13. Buettner R, et al. An alternatively spliced form of AP-2 encodes a negative regulator of transcriptional activation by AP-2. Mol. Cell Biol 13:4174-4185 (1993).

14. Chiao P J, et al. Elevated expression of the human ribosomal S2 gene in human tumors. Molecular Carcinogenesis 5:219-231 (1992).

15. Clark P, et al. The CN2 induction algorithm. Machine Learning 3:261-283 (1989).

16. Coleman M P, et al. Trends in cancer incidence and mortality. Lyon, France: IARC Scientific Publications 121: 477-498 (1993).

17. Deyo J, et al. A novel protein expressed at high cell density but not during growth arrest. DNA and Cell Biol 17:437-447 (1998).

18. Draghici S. The Constraint Based Decomposition, accepted for publication in Neural Networks, to appear (2001).

19. Einhorn, N. et al. Prospective evaluation of serum CA 125 levels for early detection of ovarian cancer. Obstet Gynecol 80:14-18 (1992).

20. Golub T R, et al. Molecular classification of cancer: class discovery and class prediction by gene expression monitoring. Science 286:531-537 (1999).

21. Gotlieb W H, et al. Presence of interteukins in the ascites of patients with ovarian and other intrabdominal cancers. Cytokine 4:385-390 (1992).

22. Greenlee R T, et al. Cancer Statistics. CA Cancer J Clin 50:7-33 (2000).

23. Heath, S. et al. Induction of oblique decision tree. In IJCAI-93. Washington, D.C. (1993).

24. Hogdall EV, et al. Predictive values of serum tumour markers tetranectin, OVX1, CASA and CA125 in patients with a pelvic mass. Int J serum tumour markers tectranectin, OVX1, CASA and CA125 in patients with a pelvic mass. Int J Cancer 89:519-523 (2000).

25. Holschneider C H, et al. Ovarian cancer: epidemiology, biology, and prognostic factors. Semin Surg Oncol 1:3-10 (2000).

26. Houts T M: Improved 2-Color Normalization For Microarray Analyses Employing Cyanine Dyes, CAMDA (2000). Critical Assessment of Techniques for Microarray Data Mining. Duke University Medical Center, Dec. 18-19 (2000).

27. Jacobs I J, et al. Potential screening tests for ovarian cancer, in Sharp F, Mason W P, Leake R E (eds). Ovarian Cancer. London, Chapman and Hall Medical, 197-205 (1997).

28. Jacobs, I. Et al. Multimodal approach to screening for ovarian cancer. Lancet I 268-271 (1988).

29. Jacobs I, et al. The CA 125 tumor-associated antigen: a review of the literature. Hum Reprod 4:1-12 (1989).

30. Kacinski B M et al. Macrophage colony-stimulating factor is produced by human ovarian and endometrial adenocarcinoma-derived cell lines and is present at abnormally high levels in the plasma of ovarian carcinoma patients with active disease. Cancer Cells 7:333-337 (1989).

31. Kerr, Martin, Churchill. Analysis of variance for gene expression microarray data. Journal of Computational Biology (2000).

32. Kim, S Y et al. Coordinate Control of Growth and Cytokeratin 13 Expression by Retinoic Acid. Molecular Carcinogenesis 16:6-11 (1996).

33. Kohonen T. Learning vector quantization. Neural Networks, 1 (suppl.1):303 (1988).

34. Kohonen T. Learning vector quantization. In the handbook of brain theory and neural networks pp.537-540. Cambridge Mass.: MIT press (1995).

35. MacBeath G. et al. Printing proteins as microarrays for high-throughput function determination. Science 289:1760-3 (2000).

36. Murthy K. On growing better decision trees from data. Unpublished doctoral dissertation. John Hopkins University (1995).

37. Musavi M. et al. On the training of radial basis functions classifiers. Neural Networks 5:595-603 (1992).

38. Patsner B. et al. Comparison of serum CA 125 and lipid associated sialic acid (LASA-P) in monitoring patients with invasive ovarian adenocarcinoma. Gynecol Oncol 30(1): 98-103 (1988).

39. Peng Y S, et al. ARHI is the center of allelic deletion on chromosome lp31 in ovarian and breast cancers. Int J Cancer 86:690-4 (2000).

40. Precup D, et al. Classification using $/Phi$-machines and constructive function approximation. In Proc. 15th International Conf. On Machine Learning, pages 439-444. Morgan Kaufmann, San Francisco, Calif. (1998).

41. Poggio T, et al. Networks for approximation and learning. Proceedings of IEEE 78(9):1481-149 (1990).

42. Quinlan J R: C4.5: Programs for machine learning, Morgan-Kaufmann (1993).

43. Rumelhart, D E, et al. Learning internal representations by error backpropagation. Parallel Distributed Processing: Explorations in the Microstructures of Cognition, MIT Press/Bradford Books (1986).

44. Schwartz P E, et al. Circulating tumor markers in the monitoring of gynecologic malignancies. Cancer 60:353-361 (1987).

45. Schmittgen T D et al. Quantitative reverse transcription-polymerase chain reaction to study mRNA decay: comparison of endpoint and real-time methods. Anal Biochem, 285:194-204 (2000).

46. Sonoda K, Nakashima M, Kaku T, Kamura T, Nakano H, Watanabe T. A novel tumor-associated antigen expressed in human uterine and ovarian carcinomas. Cancer 1996 77:1501-9, 47. Nakashima M, Sonoda K, Watanabe T. Inhibition of cell growth and induction of apoptotic cell death by the human tumor-associated antigen RCAS1. Nat Med. 1999 5:938-42.

48. Lindstrom M S, Klangby U, Wiman K G. p14ARF homozygous deletion or MDM2 overexpression in Burkitt lymphoma lines carrying wild type 53. Oncogene. 20(17):2171-7, 2001.

What is claimed is:

1. A method of detecting informative markers of early stage cancer by:

differentially biopanning sera obtained from normal individuals and patients with early stage cancer against epitope-expressing phage display libraries;

obtaining epitope bearing clones displaying reactivity to antibodies present in sera of patients with early stage cancer but not in sera of normal individuals, including the step of identifying and excluding the sera of normal individuals that react strongly but nonspecifically to epitope bearing clones, wherein the step of excluding the sera of normal individuals which react strongly but nonspecifically to epitope bearing clones further includes the step of excluding sera which show a unimodal pattern of dual fluorescence reaction with epitope bearing clones, where a first color indicates reaction with human immunoglobulin and a second color indicates reaction to phage capsid proteins;

identifying all epitopes that are specific to patients with early stage cancer as informative markers of early stage cancer; and including all epitopes identified as informative markers in a microarray assay designed to detect early stage cancer.

* * * * *